United States Patent
Chau et al.

(10) Patent No.: US 8,252,051 B2
(45) Date of Patent: Aug. 28, 2012

(54) METHOD OF IMPLANTING A PROSTHETIC VALVE IN A MITRAL VALVE WITH PULMONARY VEIN ANCHORING

(75) Inventors: Mark Chau, Aliso Viejo, CA (US); Seung Yi, Mission Viejo, CA (US); Philip Corso, Irvine, CA (US); Michael J. Popp, Irvine, CA (US); Kevin Golemo, Mission Viejo, CA (US); Jane Olin, Irvine, CA (US); Son V. Nguyen, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/007,378

(22) Filed: Jan. 14, 2011

(65) Prior Publication Data

US 2011/0112632 A1    May 12, 2011

Related U.S. Application Data

(63) Continuation of application No. 12/393,010, filed on Feb. 25, 2009, now abandoned.

(51) Int. Cl.
*A61F 2/24* (2006.01)
(52) U.S. Cl. ...... 623/2.12; 623/2.1; 623/2.13; 623/2.14; 623/2.17
(58) Field of Classification Search .......... 623/2.1–2.19; *A61F 2/24*
See application file for complete search history.

(56) References Cited

U.S. PATENT DOCUMENTS

| 3,409,013 A | 11/1968 | Berry |
| 3,472,230 A | 10/1969 | Fogarty et al. |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |

(Continued)

FOREIGN PATENT DOCUMENTS

DE    2246526    3/1973

(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.

(Continued)

*Primary Examiner* — Thomas J Sweet
*Assistant Examiner* — Jason-Dennis Stewart
(74) *Attorney, Agent, or Firm* — David L. Hauser; Pui Tong Ho

(57) ABSTRACT

A method of implanting a prosthetic mitral valve assembly is disclosed. The prosthetic mitral valve assembly includes a stent and valve combination. The prosthetic mitral valve assembly is provided with an anchoring portion adapted to be positioned in the left atrium. In one embodiment, the anchoring portion includes at least one anchoring arm sized for placement in a pulmonary vein. The stent is radially expandable so that it can expand into position against the walls of the left atrium and accommodate a wide range of anatomies. Contact between the stent and the native tissue in the left atrium reduces paravalvular leakage and prevents migration of the stent once in place.

19 Claims, 15 Drawing Sheets

U.S. PATENT DOCUMENTS

| | | |
|---|---|---|
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian |
| 6,302,906 B1 | 10/2001 | Goicoechea et al. |
| 6,350,277 B1 | 2/2002 | Kocur |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,569,196 B1 | 5/2003 | Vesely et al. |
| 6,582,462 B1 | 6/2003 | Andersen et al. |
| 6,605,112 B1 | 8/2003 | Moll |
| 6,730,118 B2 | 5/2004 | Spenser et al. |
| 6,733,525 B2 | 5/2004 | Yang et al. |
| 6,830,584 B1 | 12/2004 | Seguin |
| 6,893,460 B2 | 5/2005 | Spenser et al. |
| 6,908,481 B2 | 6/2005 | Cribier |
| 7,018,406 B2 | 3/2006 | Seguin et al. |
| 7,276,078 B2 | 10/2007 | Spenser et al. |
| 7,276,084 B2 | 10/2007 | Yang et al. |
| 7,374,571 B2 | 5/2008 | Pease et al. |
| 7,393,360 B2 | 7/2008 | Spenser et al. |
| 7,442,204 B2 | 10/2008 | Schwammental et al. |
| 7,462,191 B2 | 12/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0212454 A1 | 11/2003 | Scott et al. |
| 2004/0039436 A1 | 2/2004 | Spenser et al. |
| 2004/0186565 A1 | 9/2004 | Schreck |
| 2004/0260389 A1 | 12/2004 | Case et al. |
| 2005/0177224 A1 | 8/2005 | Fogarty et al. |
| 2005/0203616 A1 | 9/2005 | Cribier |
| 2005/0234546 A1 | 10/2005 | Nugent et al. |
| 2006/0025857 A1 | 2/2006 | Bergheim et al. |
| 2006/0149350 A1 | 7/2006 | Patel et al. |
| 2006/0167543 A1 | 7/2006 | Bailey et al. |
| 2006/0229719 A1 | 10/2006 | Marquez et al. |
| 2006/0241745 A1* | 10/2006 | Solem ........................ 623/2.18 |
| 2006/0259137 A1 | 11/2006 | Artof et al. |
| 2008/0154355 A1 | 6/2008 | Benichou et al. |
| 2008/0183273 A1 | 7/2008 | Mesana et al. |
| 2008/0255660 A1 | 10/2008 | Guyenot et al. |
| 2009/0234435 A1 | 9/2009 | Johnson et al. |
| 2009/0276040 A1* | 11/2009 | Rowe et al. ................. 623/2.18 |
| 2010/0168778 A1* | 7/2010 | Braido ........................ 606/185 |

FOREIGN PATENT DOCUMENTS

| | | |
|---|---|---|
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049814 | 4/2002 |

| | | |
|---|---|---|
| DE | 10049815 | 4/2002 |
| EP | 0103546 | 3/1984 |
| EP | 0144167 | 6/1985 |
| EP | 0597967 | 12/1994 |
| EP | 0592410 | 10/1995 |
| EP | 0850607 | 7/1998 |
| EP | 1057460 | 12/2000 |
| EP | 1088529 | 4/2001 |
| EP | 1570809 | 9/2005 |
| FR | 2788217 | 7/2007 |
| GB | 2056023 | 3/1981 |
| SU | 1271508 | 11/1986 |
| WO | WO 91/17720 | 11/1991 |
| WO | WO 92/17118 | 10/1992 |
| WO | WO 93/01768 | 2/1993 |
| WO | WO 97/24080 | 7/1997 |
| WO | WO 98/29057 | 7/1998 |
| WO | WO 99/33414 | 7/1999 |
| WO | WO 99/40964 | 8/1999 |
| WO | WO 99/47075 | 9/1999 |
| WO | WO 00/18333 | 4/2000 |
| WO | WO 00/41652 | 7/2000 |
| WO | WO 00/47139 | 8/2000 |
| WO | WO 01/35878 | 5/2001 |
| WO | WO 01/49213 | 7/2001 |
| WO | WO 01/54624 | 8/2001 |
| WO | WO 01/54625 | 8/2001 |
| WO | WO 01/62189 | 8/2001 |
| WO | WO 01/64137 | 9/2001 |
| WO | WO 01/76510 | 10/2001 |
| WO | WO 02/22054 | 3/2002 |
| WO | WO 02/36048 | 5/2002 |
| WO | WO 02/41789 | 5/2002 |
| WO | WO 02/43620 | 6/2002 |
| WO | WO 02/47575 | 6/2002 |
| WO | WO 02/49540 | 6/2002 |
| WO | WO 03/047468 | 6/2003 |
| WO | WO 2005/087140 | 9/2005 |
| WO | WO 2006/014233 | 2/2006 |
| WO | WO 2006/034008 | 3/2006 |
| WO | WO 2008/005405 | 1/2008 |
| WO | WO 2008/035337 | 3/2008 |
| WO | WO 2008/147964 | 12/2008 |
| WO | WO 2008/150529 | 12/2008 |

OTHER PUBLICATIONS

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Serruys, P.W., et al., "Stenting of Coronary Arteries. Are we the Sorcerer's Apprentice?," European Heart Journal (1989) 10, 774-782, pp. 37-45, Jun. 13, 1989.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili..., Jul. 29, 2009, 2 pages.

Urban, M.D., Philip, "Coronary Artery Stenting," Editions Médecine et Hygiène, Genève, 1991, pp. 5-47.

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Wheatley, M.D., David J., "Valve Prostheses," Rob & Smith's Operative Surgery, Fourth Edition, pp. 415-424, Butterworths 1986.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Uchida, Barry T., et al., "Modifications of Gianturco Expandable Wire Stents," AJR:150, May 1988, Dec. 3, 1987, pp. 1185-1187.

Selby, M.D., J. Bayne, "Experience with New Retrieval Forceps for Foreign Body Removal in the Vascular, Urinary, and Biliary Systems," Radiology 1990; 176:535-538.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Al Zaibag, Muayed, et al., "Percutaneous Balloon Valvotomy in Tricuspid Stenosis," British Heart Journal, Jan. 1987, vol. 57, No. 1, pp. 51-53.

Lawrence, Jr., M.D., David D., "Percutaneous Endovascular Graft: Experimental Evaluation," Radiology 1897; 163: 357-360.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Sigwart, Ulrich, "An Overview of Intravascular Stents: Old and New," Chapter 48, Textbook of Interventional Cardiology, $2^{nd}$ Edition, W.B. Saunders Company, Philadelphia, PA, © 1994, 1990, pp. 803-815.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Ross, F.R.C.S., D.N., "Aortic Valve Surgery," Guy's Hospital, London, pp. 192-197, approximately 1968.

Rashkind, M.D., William J., "Creation of an Atrial Septal Defect Withoput Thoracotomy," the Journal of the American Medical Association, vol. 196, No. 11, Jun. 13, 1966, pp. 173-174.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

Curriculum Vitae of Robert A. Ersek, M.D., FACS, Jul. 10, 2009, http://www.ersek.com/rae-cv.htm.

* cited by examiner

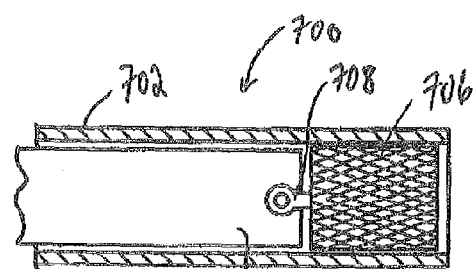
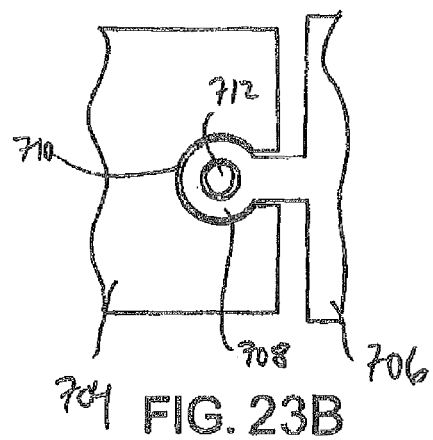
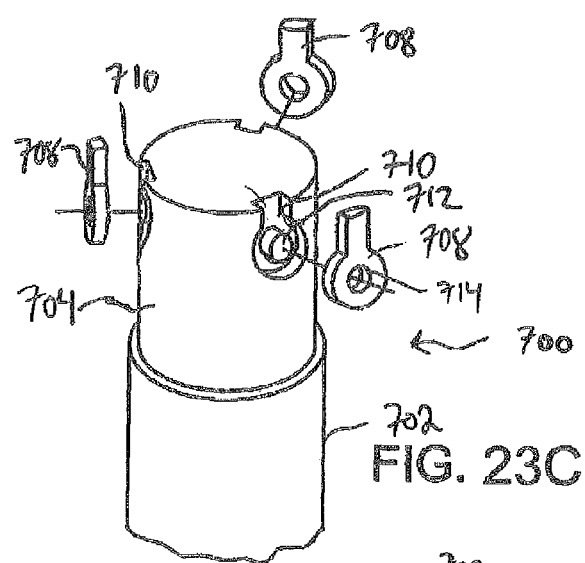
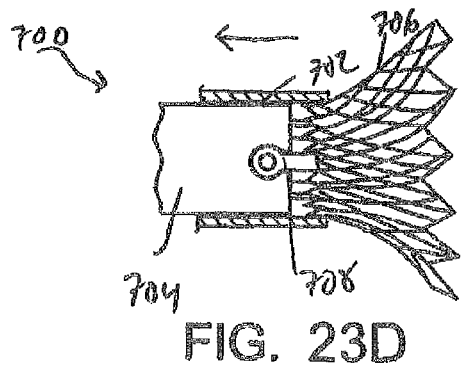
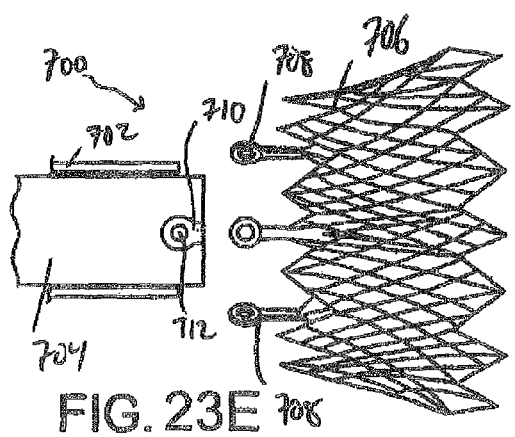

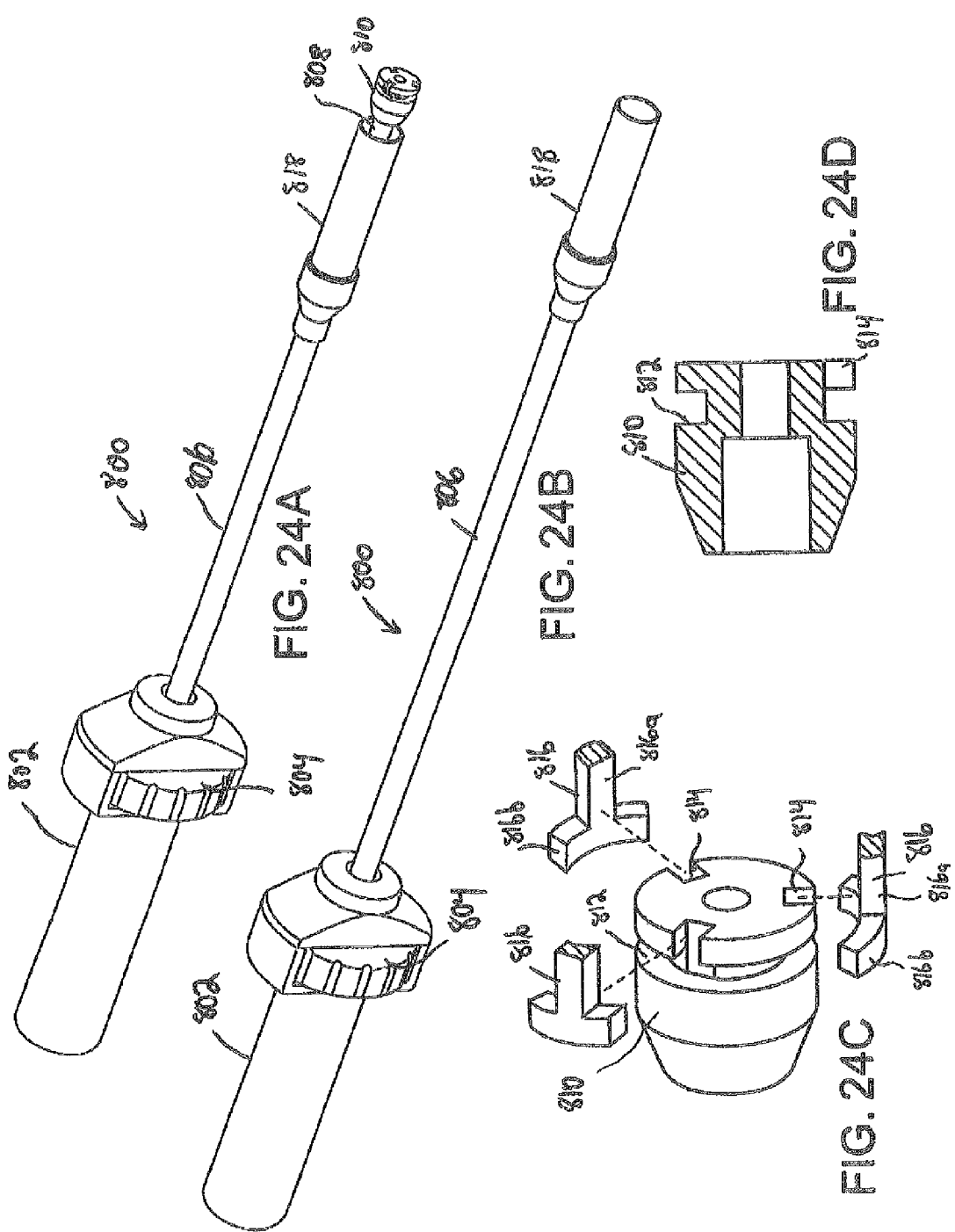

METHOD OF IMPLANTING A PROSTHETIC VALVE IN A MITRAL VALVE WITH PULMONARY VEIN ANCHORING

CROSS-REFERENCE TO RELATED APPLICATIONS

This application is a continuation of co-pending U.S. patent application Ser. No. 12/393,010, filed Feb. 25, 2009.

FIELD

The present disclosure concerns a prosthetic mitral heart valve and a method for implanting such a heart valve.

BACKGROUND

Prosthetic cardiac valves have been used for many years to treat cardiac valvular disorders. The native heart valves (such as the aortic, pulmonary, tricuspid and mitral valves) serve critical functions in assuring the forward flow of an adequate supply of blood through the cardiovascular system. These heart valves can be rendered less effective by congenital, inflammatory, infectious conditions or disease. Such damage to the valves can result in serious cardiovascular compromise or death. For many years the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted.

Another known technique for implanting a prosthetic aortic valve is a transapical approach where a small incision is made in the chest wall of a patient and the catheter is advanced through the apex (i.e., bottom tip) of the heart. Transapical techniques are disclosed in U.S. Patent Application Publication No. 20070112422, which is hereby incorporated by reference. Like the transvascular approach, the transapical approach includes a balloon catheter having a steering mechanism for delivering a balloon-expandable prosthetic heart valve through an introducer to the aortic annulus. The balloon catheter includes a deflecting segment just proximal to the distal balloon to facilitate positioning of the prosthetic heart valve in the proper orientation within the aortic annulus.

The above techniques and others have provided numerous options for high-risk patients with aortic valve stenosis to avoid the consequences of open heart surgery and cardiopulmonary bypass. While procedures for the aortic valve are well-developed, such procedures are not necessarily applicable to the mitral valve.

Mitral valve repair has increased in popularity due to its high success rates, and clinical improvements noted after repair. Unfortunately, a significant percentage of patients still receive mitral valve replacement due to stenosis or anatomical limitations. There are a number of technologies aimed at making mitral repair a less invasive procedure. These technologies range from iterations of the Alfieri stitch procedure to coronary sinus-based modifications of mitral anatomy to subvalvular placations or ventricular remodeling devices, which would incidentally correct mitral regurgitation.

However, for mitral valve replacement, few less-invasive options are available. There are approximately 60,000 mitral valve replacements (MVR) each year and it is estimated that another 60,000 patients should receive a MVR due to increased risk of operation and age. The large majority of these replacements are accomplished through open-heart surgery. One potential option for a less invasive mitral valve replacement is disclosed in U.S. Patent Application 2007/0016286 to Herrmann. However, the stent disclosed in that application has a claw structure for attaching the prosthetic valve to the heart. Such a claw structure could have stability issues and limit consistent placement of a transcatheter mitral replacement valve.

Accordingly, further options are needed for less-invasive mitral valve replacement.

SUMMARY

A prosthetic mitral valve assembly and method of inserting the same is disclosed.

In certain disclosed embodiments, the prosthetic mitral valve assembly includes a stent and valve combination. The stent is designed so that the anchoring portion is positioned above the annulus of the mitral valve and in the left atrium. The stent is radially expandable and can press against the walls of the left atrium with a pressure or friction fit to accommodate a wide range of anatomies.

In one embodiment, the entire prosthetic mitral valve assembly is positioned above the native annulus so that the native mitral valve leaflets and chordae are preserved. As a result, the prosthetic mitral valve and the native mitral valve function in series.

In another embodiment, a majority of the prosthetic mitral valve assembly is implantable in the left atrium. However, a lower portion of the mitral valve assembly extends into the native mitral valve rendering the native mitral valve incompetent. Contact between the stent and the native tissue in the left atrium reduces paravalvular leakage and prevents migration of the stent once in place.

In another embodiment, a majority of the prosthetic mitral valve assembly is implantable in the left atrium. A lower tapered portion partially extends into the native mitral valve but does not extend into the left ventricle in order to ensure that the chordae tendineae are not contacted by portions of the stent. This embodiment can improve cardiac performance while preserving the function of the chordae tendineae.

In yet another embodiment, the mitral valve assembly includes additional anchoring with one or more anchoring arms that contact an upper portion of the atrium or the pulmonary veins. The anchoring arms utilize the natural anatomy of the patient's heart in order to resist against upward migration of the assembly. Other embodiments also use the upper portion of the atrium or the pulmonary veins without using anchoring arms.

The foregoing and other objects, features, and advantages of the invention will become more apparent from the following detailed description, which proceeds with reference to the accompanying figures.

BRIEF DESCRIPTION OF THE DRAWINGS

FIG. 23A is a cross-sectional view of the distal end portion of a delivery apparatus that can be used to implant a prosthetic mitral valve in the heart, according to another embodiment.

FIG. 23B is an enlarged view of a portion of FIG. 23A showing the connection between the valve stent and the distal end of the delivery apparatus.

FIG. 23C is a perspective view of the delivery apparatus of FIG. 23A.

FIGS. 23D and 23E illustrate the valve being deployed from the delivery apparatus shown in FIG. 23A.

FIG. 24A is a perspective view of a delivery apparatus for a prosthetic valve shown with the sheath of the delivery apparatus in a retracted position for deploying the valve, according to another embodiment.

FIG. 24B is a perspective view of the delivery apparatus of FIG. 24A shown with the sheath in a distal position for covering the valve during valve delivery.

FIG. 24C is an enlarged, perspective view of an end piece of the delivery apparatus of FIG. 24A and three posts of a valve stent that are received within respective recesses in the end piece.

FIG. 24D is a cross-sectional view of the end piece shown in FIG. 24C.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but can optionally contain C or other components other than A and B. A device that includes or comprises A or B may contain A or B or A and B, and optionally one or more other components such as C.

Figure 1:
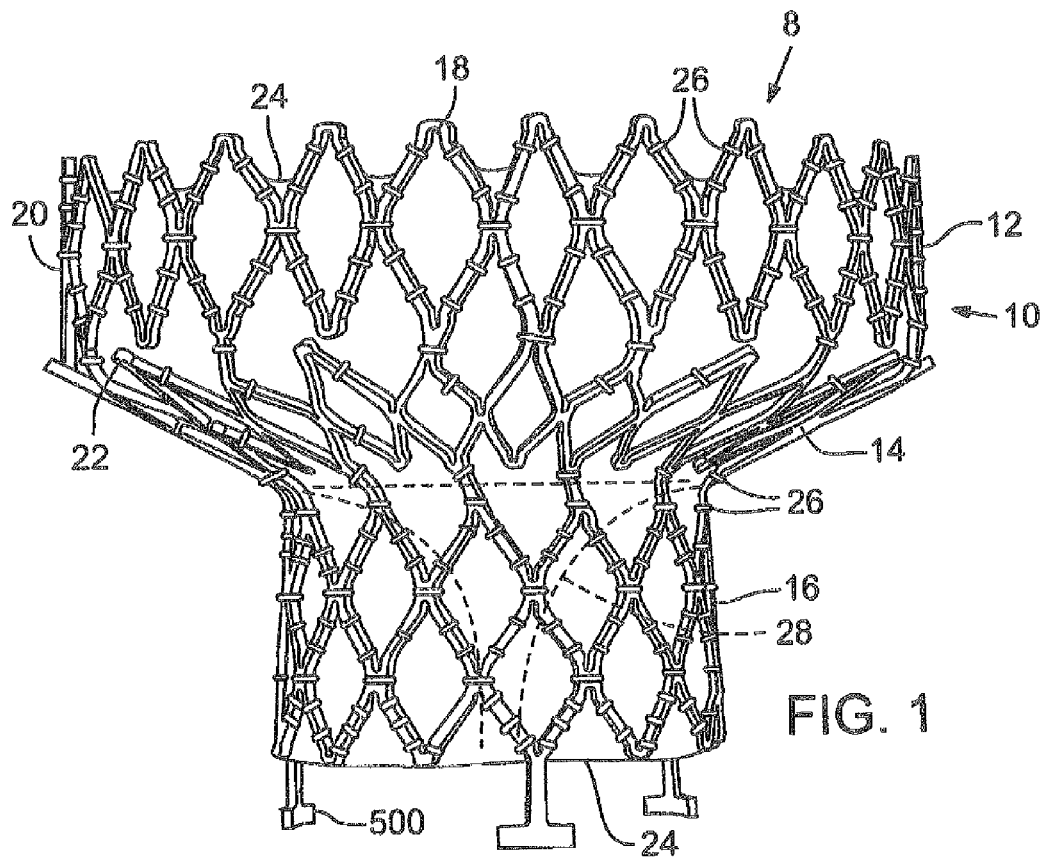
FIG. 1 is a perspective view of an embodiment of a mitral valve assembly that can be inserted into the native mitral valve, but that is anchored above a native annulus.

FIG. 1 is a perspective view of a mitral valve assembly 8 that can be used as a mitral valve replacement. The mitral valve assembly 8 includes a radially compressible and expandable stent 10 having an upper portion 12 with an enlarged end, a tapered middle portion 14 and a lower portion 16 with a circumference that is less than that of the upper portion 12. The stent can be an inverted bell shape, but other shapes can be used. Additionally, although only the middle portion 14 is shown as tapered, the stent 10 can have a continuous taper from the upper portion 12 to the lower portion 16. An upper edge 18 of the stent 10 can be a sawtoothed or scalloped pattern to maximize a surface area with which the stent connects to the native tissue. Alternatively, the upper edge can be a straight edge, or some other pattern.

The stent 10 can have a self-expanding frame 20 formed from a shape memory material, such as, for example, Nitinol. The illustrated embodiment shows that the stent frame 20 can include metal strips or struts arranged in a lattice pattern, but other patterns can be used. In certain embodiments the stent frame 20 can be made of stainless steel or any other suitable materials. The tapered middle portion 14 can have certain of the metal strips intentionally disconnected from the upper portion 12 in order to create prongs 22 extending outwardly from the stent 10 that assist in holding the prosthetic mitral valve assembly to the native tissue. Alternatively, barbs (not shown) can be separately attached to the stent in order to create the prongs. One advantage of the illustrated embodiment is that the prongs 22 are formed from the frame itself or integral with the frame, rather than being separately added. In other embodiments (not shown), the disconnected metal strips can be connected, if the prongs 22 are not desired. In such a case, each cell of the tapered portion 14 can be connected to the upper portion 12. A biocompatible sheet or fabric material 24 can be connected to the inner surface of the frame 20 to form an inner layer or envelope covering the open portions of the stent to reduce paravalular leakage. The sheet or fabric 24 can be made from synthetic materials, such as a polyester material or a biocompatible polymer. One example of a polyester material is polyethylene terephthalate (PET). Alternative materials can be used. For example, the sheet or fabric can be made from biological matter, such as natural tissue, pericardial tissue (e.g., bovine, porcine or equine pericardium) or other biological tissue. The sheet or fabric 24 can be connected to the frame 20 by sutures, such as shown at 26.

As shown in dashed lines, the mitral valve assembly 8 includes a valve 28 positioned in the lower portion 16 of the stent 10. The valve 28 can have a leafed-valve configuration, such as a bicuspid valve or tricuspid valve configuration. The valve 28 can be connected to the frame 20 using, for example, sutures 26 or other suitable connection techniques well-known in the art. Alternatively, the valve 18 can be a mechanical type valve, rather than a leafed type valve. Still further, the valve 18 can be made from biological matter, such as natural tissue, pericardial tissue (e.g., bovine, porcine or equine pericardium), a harvested natural valve, or other biological tissue. Alternatively, the valve can be made from biocompatible synthetic materials (e.g., biocompatible polymers), which are well known in the art. Blood flow through the valve proceeds in a direction from the upper portion 12 to the lower portion 16. Those skilled in the art will recognize that the particular type of valve used is not of importance and a wide variety of valves can be used.

The features of FIG. 1 can be used in any of the embodiments herein described. Thus, for each of the embodiments below, the materials that can be used for the valve, the biocompatible sheet, and the frame will not be repeated and should be assumed to be at least those described in FIG. 1. Additionally, the prongs and barbs of FIG. 1 can be used in any of the embodiments described herein.

Figure 2:
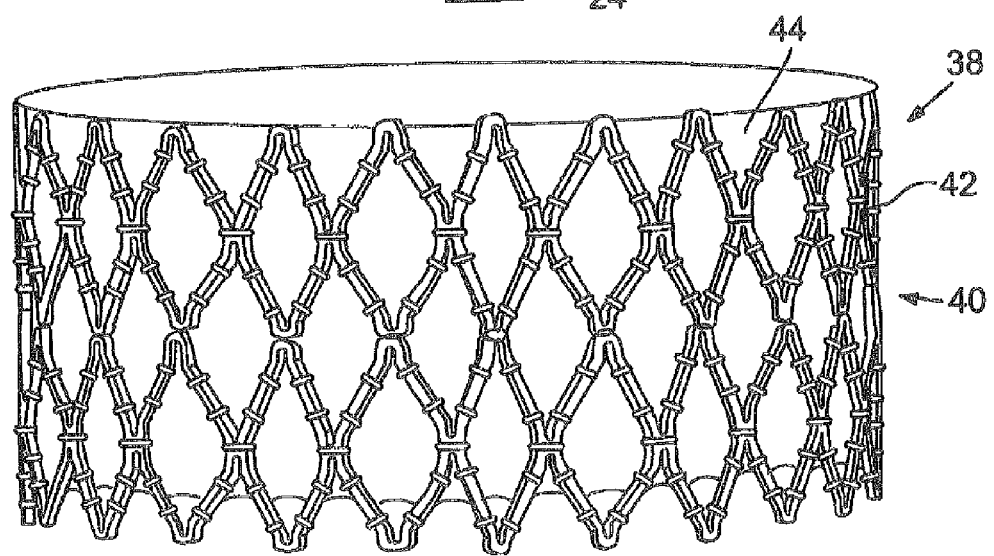
FIG. 2 is a perspective view of another embodiment of a mitral valve assembly that can work in series with the native mitral valve.

FIG. 2 is a perspective view of another embodiment of a mitral valve assembly 38 sized for atrial implantation and designed to work in series with the native mitral valve, as further described below. The mitral valve assembly 38 includes a stent 40 having a frame 42 supporting a biocompatible sheet or fabric 44, both of which are similar to those already described. The stent supports a valve (not visible in FIG. 2) attached to and sized to be compatible with the frame 42. Any of the valves already described can be used. However, because of the location of the stent 40 in the atrium, the valve can be larger than that of FIG. 1.

Figure 3:
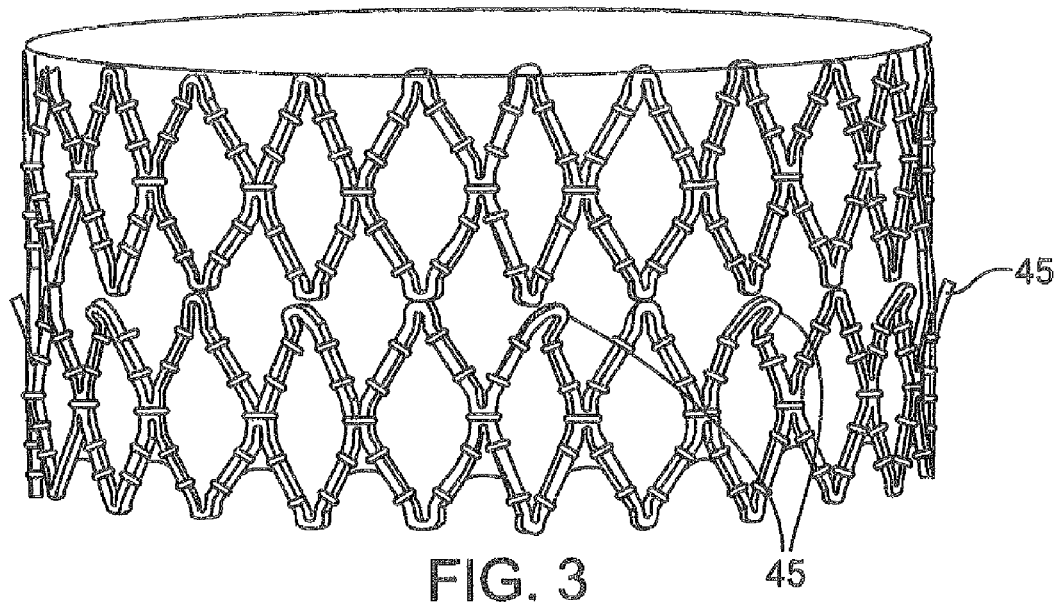
FIG. 3 is a perspective view of another embodiment of a mitral valve assembly having outwardly extending prongs for anchoring the assembly.

FIG. 3 is a perspective view of another embodiment of a mitral valve assembly, which is the same as FIG. 2, but with prongs 45 added. More particularly, cells of the frame's lattice structure are left intentionally disconnected from adjacent cells and are bent outwardly to create the prongs 45. FIG. 3 is illustrative that prongs can be added to any of the embodiments described herein. Alternatively, the prongs can be removed from any of the embodiments simply by leaving the lattice structure fully connected. Furthermore, in any of the embodiments herein described, barbs (not shown) can be separately attached to the stent in order to create the prongs.

Figure 4:
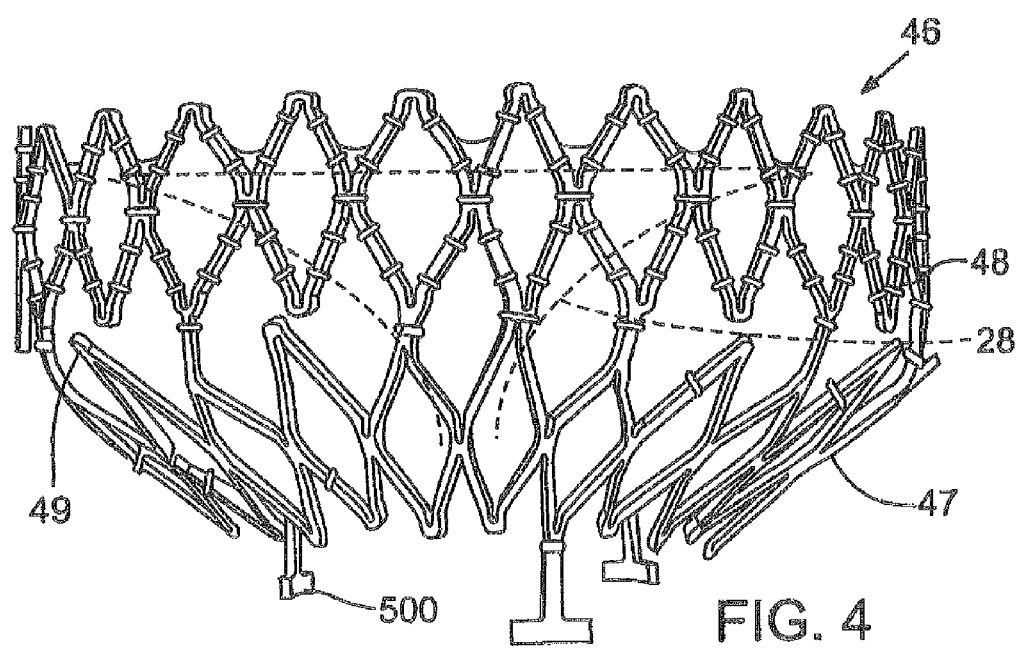
FIG. 4 is a perspective view of another embodiment of a mitral valve assembly that can extend partially into the native mitral valve.

FIG. 4 shows another embodiment 46 of a mitral valve assembly having an upper portion and a lower tapered portion 47. The mitral valve assembly includes a frame 48 having a lattice structure with certain cells of the lattice left intentionally disconnected to create outwardly extending prongs 49, similar to those described in relation to FIG. 1 (the prongs can be eliminated or separate barbs added, as already described above). The lower tapered portion 47 partially extends into the native mitral valve, but does not extend into the left ventricle, which can improve cardiac performance and ensure that the chordae tendineae are not damaged by the assembly.

Figure 5:
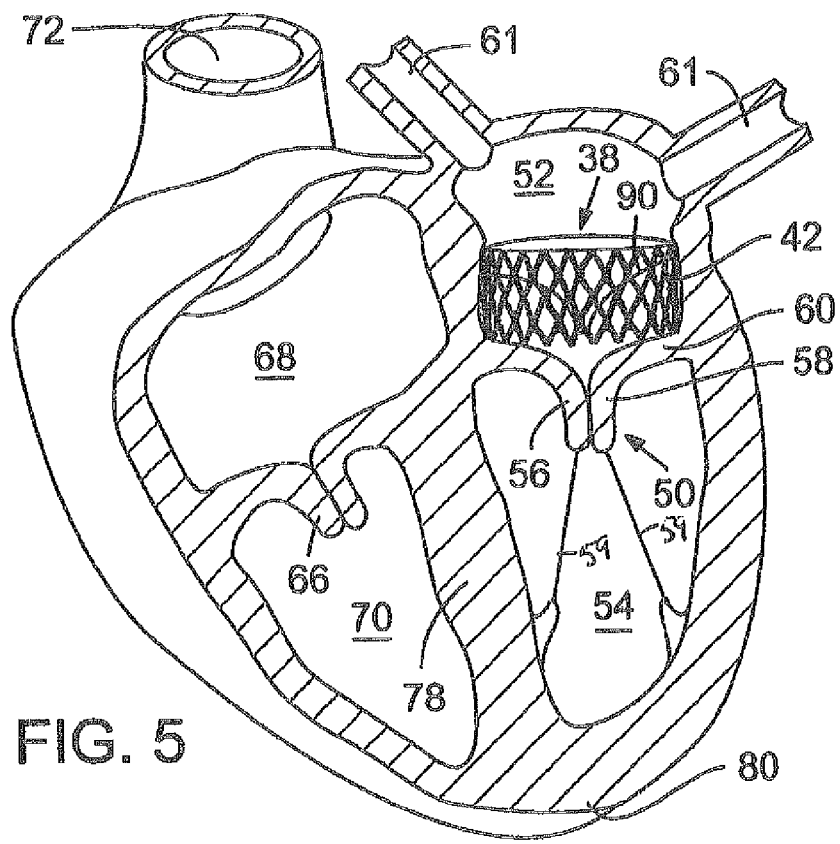
FIG. 5 is a cross-sectional view of a heart with the mitral valve assembly of FIG. 2 mounted in the left atrium.

FIG. 5 shows a cross-sectional view of a heart with the prosthetic mitral-valve assembly 38 inserted into a patient's heart. For purposes of background, the four-chambered heart is explained further. On the left side of the heart, the native mitral valve 50 is located between the left atrium 52 and left ventricle 54. The mitral valve 50 generally comprises two leaflets, an anterior leaflet 56 and a posterior leaflet 58 that are attached to the left ventricle by chordae tendineae 59, which prevent eversion of the leaflets into the left atrium. The mitral valve leaflets are attached to a mitral valve annulus 60, which is defined as the portion of tissue surrounding the mitral valve orifice. More specifically, the mitral annulus constitutes the anatomical junction between the ventricle and the left atrium, and serves an insertion site for the leaflet tissue. The left atrium 52 receives oxygenated blood from the pulmonary veins 61 (only two of four pulmonary veins are shown for simplicity). The oxygenated blood that is collected in the left atrium 52 enters the left ventricle 54 through the mitral valve 50. Contraction of the left ventricle 54 forces blood through the left ventricular outflow tract and into the aorta (not shown). As used herein, the left ventricular outflow tract (LVOT) is intended to generally include the portion of the heart through which blood is channeled from the left ventricle to the aorta. On the right side of the heart, the tricuspid valve 66 is located between the right atrium 68 and the right ventricle 70. The right atrium 68 receives blood from the superior vena cava 72 and the inferior vena cava (not shown). The superior vena cava 72 returns de-oxygenated blood from the upper part of the body and the inferior vena cava returns de-oxygenated blood from the lower part of the body. The right atrium 68 also receives blood from the heart muscle itself via the coronary sinus. The blood in the right atrium 68 enters into the right ventricle 70 through the tricuspid valve 66. Contraction of the right ventricle forces blood through the right ventricle outflow tract and into the pulmonary arteries. The left and right sides of the heart are separated by a wall generally referred to as the septum 78. The portion of the septum that separates the two upper chambers (the right and left atria) of the heart is termed the artial (or interatrial) septum while the portion of the septum that lies between the two lower chambers (the right and left ventricles) of the heart is called the ventricular (or interventricular) septum. A healthy heart has a generally conical shape that tapers from a base to an apex 80.

The mitral valve assembly 38 is shown as positioned above the annulus 60 of the native mitral valve 50 and entirely within the left atrium. As already described, the stent 40 is radially expandable and is anchored in the atrium through a pressure or friction fit with the surrounding tissue. Through radial expansion, the frame 42 adapts to the natural anatomy of the patient's atrium. For purposes of illustration, a valve 90 is shown as visible through the biocompatible sheet 44. As shown, the native mitral valve 50 is competent and works in series with the prosthetic mitral valve assembly 38. Any regurgitant volume that passes back through the native valve in the left atrium is immediately blocked by the secondary prosthetic mitral valve assembly 38. The native valve absorbs the majority of the systolic pressure, while the prosthetic mitral valve assembly 38 receives only a fraction of the systolic pressure imparted by the regurgitant volume. As a result, the prosthetic mitral valve assembly can have improved durability and reduced risk of valve migration. Such an ability to work in series with the native mitral valve is also true of the embodiments described in FIGS. 6-10.

Figure 6:
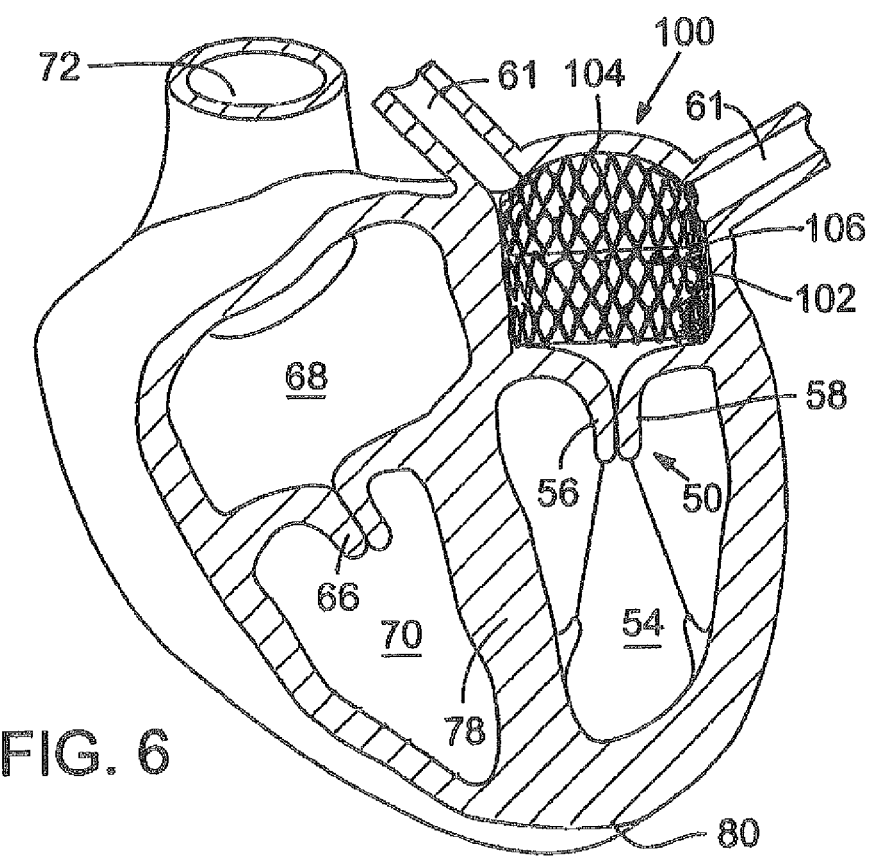
FIG. 6 is a cross-sectional view of a heart having another embodiment of the mitral valve assembly mounted in the left atrium with the mitral valve assembly extending to a roof of the atrium.

FIG. 6 shows a cross-sectional view of a heart with another embodiment of a prosthetic mitral-valve assembly 100 inserted into the atrium. In this embodiment, a stent 102 has a self-expanding frame similar to stent 40 described above. The mitral valve assembly 100 has a dome-shaped upper portion 104 that can expand to fit the natural anatomical geometry of a roof of the atrium. As a result, the mitral valve assembly 100 can expand in two dimensions, such as a horizontal direction and a vertical direction. By expanding horizontally, the mitral-valve assembly uses side walls of the atrium to anchor the assembly. By expanding vertically, the assembly expands between the annulus of the mitral valve and the roof of the atrium in order to anchor the assembly in the atrium. Thus, the roof of the atrium can exert a downward pressure on the assembly in order to prevent upward migration. A biocompatible sheet 106 extends from a bottom edge of the stent to some point below the pulmonary veins 61 so that blood flow through the pulmonary veins remains unobstructed. A valve (not shown) can be positioned at a lower end of the assembly and works in series with the native mitral valve, similar to the embodiments already described.

Figure 7:
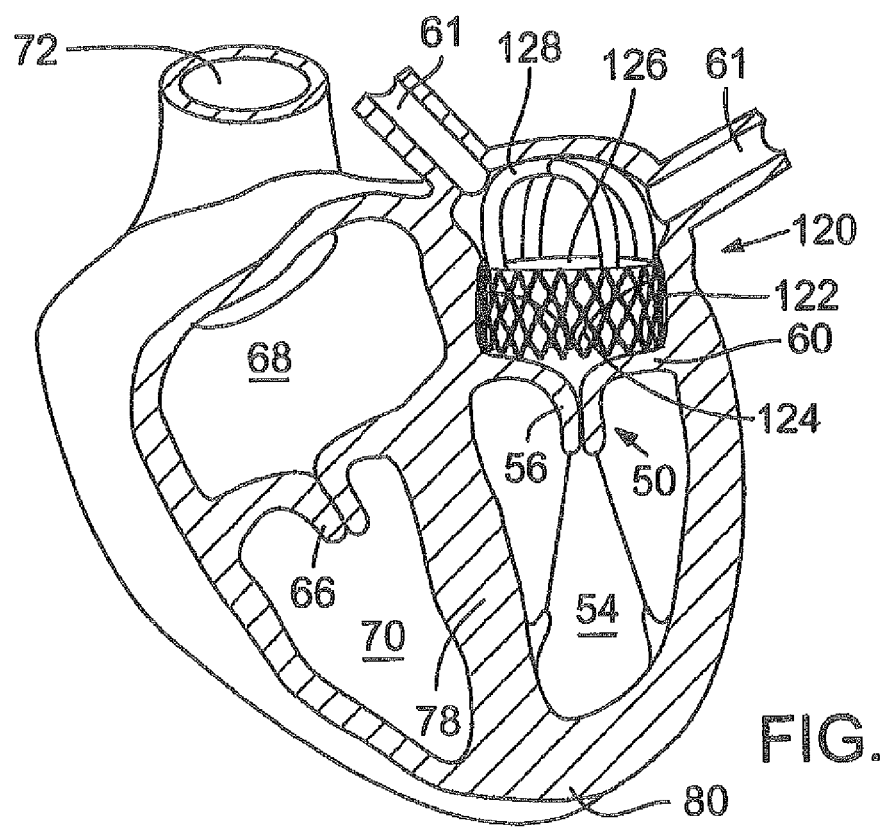
FIG. 7 is a cross-sectional view of a heart with another embodiment of the mitral valve assembly mounted in the left atrium and having at least one anchoring arm extending to a roof of the atrium.

FIG. 7 shows a cross-sectional view of a heart with another embodiment of a prosthetic mitral-valve assembly 120 inserted into the atrium and positioned above the annulus 60 of the native mitral valve 50. The assembly 120 includes a radially-expandable stent 122 that is anchored in the atrium through a pressure or friction fit. Through radial expansion, the frame of the stent adapts to the natural anatomy of the patient's atrium. A valve 124 is shown as visible through a biocompatible sheet 126. As shown, the native mitral valve 50 is competent and works in series with the prosthetic mitral valve assembly 120. Any regurgitant volume that passes by the native valve is blocked by the secondary prosthetic valve assembly. As already described, the result is an assembly with improved durability and reduced risk of valve migration. As in the other embodiments, the biocompatible sheet 126 is attached to the stent 122 in order to prevent paravalvular leakage. Four anchoring arms 128 are coupled to the stent frame 122 and are equally spaced around the frame's circumference. The opposite ends of the anchoring arms 128 are coupled together adjacent the roof of the atrium to create an open-ended dome. The anchoring arms 128 allow the mitral valve assembly 120 to expand in two dimensions, such as a horizontal direction and a vertical direction. By expanding horizontally, the mitral-valve assembly uses side walls of the atrium to anchor the assembly. By expanding vertically, the assembly expands between the annulus of the mitral valve and the roof of the atrium in order to anchor the assembly in the atrium. Thus, the roof of the atrium can exert a downward pressure on the assembly in order to prevent upward migration. Although four anchoring arms are shown, any number of anchoring arms can be used (e.g., 1, 2, 3, 5, 6, etc.) Additionally, the anchoring arms 128 can be made of a flexible metal (similar or identical to the stent) or polymer.

Figure 8:
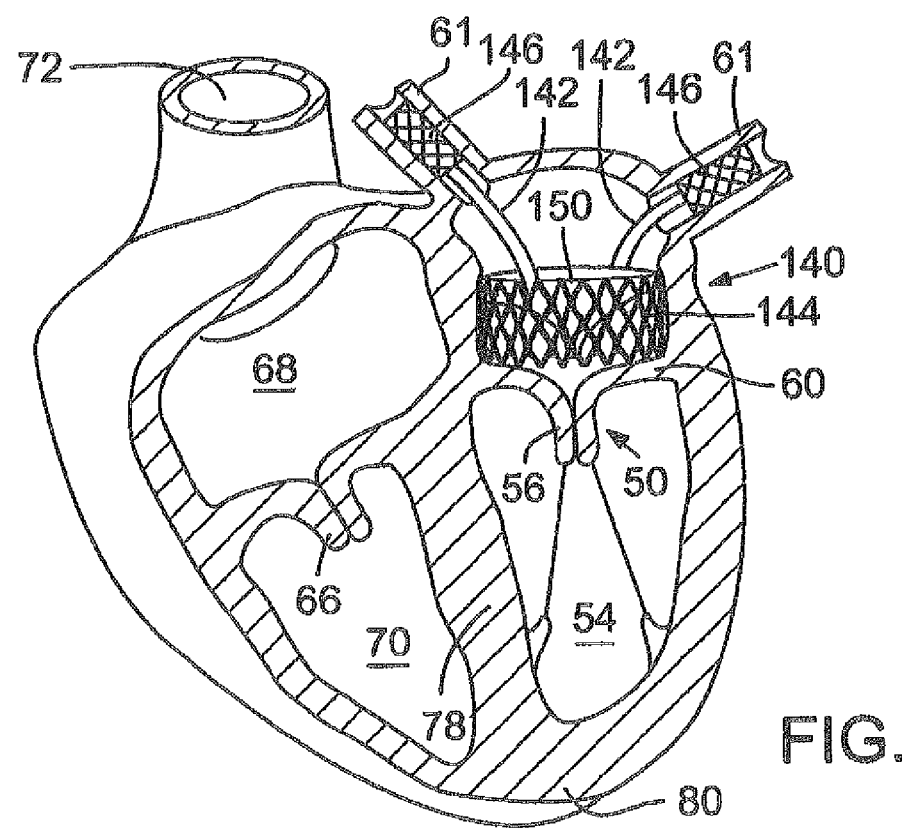
FIG. 8 is a cross-sectional view of a heart having another embodiment of the mitral valve assembly mounted in the left atrium with at least one anchoring arm extending into at least one pulmonary vein.

FIG. 8 shows a cross-sectional view of a heart with another embodiment of a prosthetic mitral-valve assembly 140 inserted into the atrium and positioned above the annulus 60 of the native mitral valve 50. This embodiment also includes anchoring arms 142, similar to FIG. 7, except the anchoring arms 142 are coupled to a stent frame 144 at one end and to one or more pulmonary veins 61 at an opposite end. To couple the anchoring arms 142 to the pulmonary veins 61, pulmonary vein stents 146 are mounted into the pulmonary veins and are coupled to one end of the anchoring arms 142. The pulmonary vein stents 146 can be made from the same material as other stents described above and can be radially expandable. Additionally, the anchoring arms 142 can be made of a flexible metal (similar or identical to the stent) or polymer. Furthermore, although two anchoring arms are shown, any number of anchoring arms can be used (e.g., 1, 2, 3, or 4). As in the other embodiments, a biocompatible sheet 150 can be attached to the stent in order to prevent paravalvular leakage.

Figure 9:
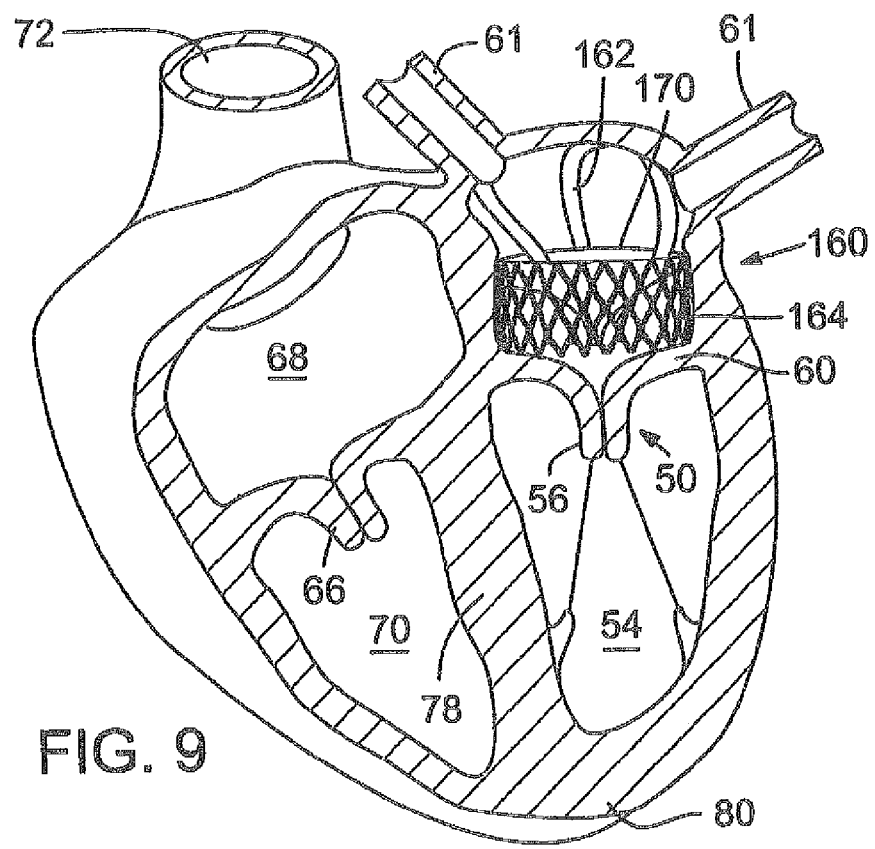
FIG. 9 is a cross-sectional view of a heart having another embodiment of the mitral valve assembly mounted in the left atrium with at least one anchoring arm extending to a roof of the atrium.

FIG. 9 shows a cross-sectional view of a heart with another embodiment of a prosthetic mitral-valve assembly 160 inserted into the atrium and positioned above the annulus 60 of the native mitral valve 50. The embodiment of FIG. 9 is similar to the embodiment of FIG. 7, but with one or more anchoring arms 162, each coupled at one end to a stent 164 and left uncoupled at an opposing end. The anchoring arms 162 can be made of a flexible metal (similar or identical to the stent) or polymer. Furthermore, although three anchoring arms are shown, any number of anchoring arms can be used (e.g., 1, 2, 3, or 4). The anchoring arms press against the roof of the atrium to provide a pressure on the stent 164 in a direction of the mitral valve to prevent upward migration of the stent. As in the other embodiments, a biocompatible sheet 170 can be attached to the stent in order to prevent paravalvular leakage.

Figure 10:
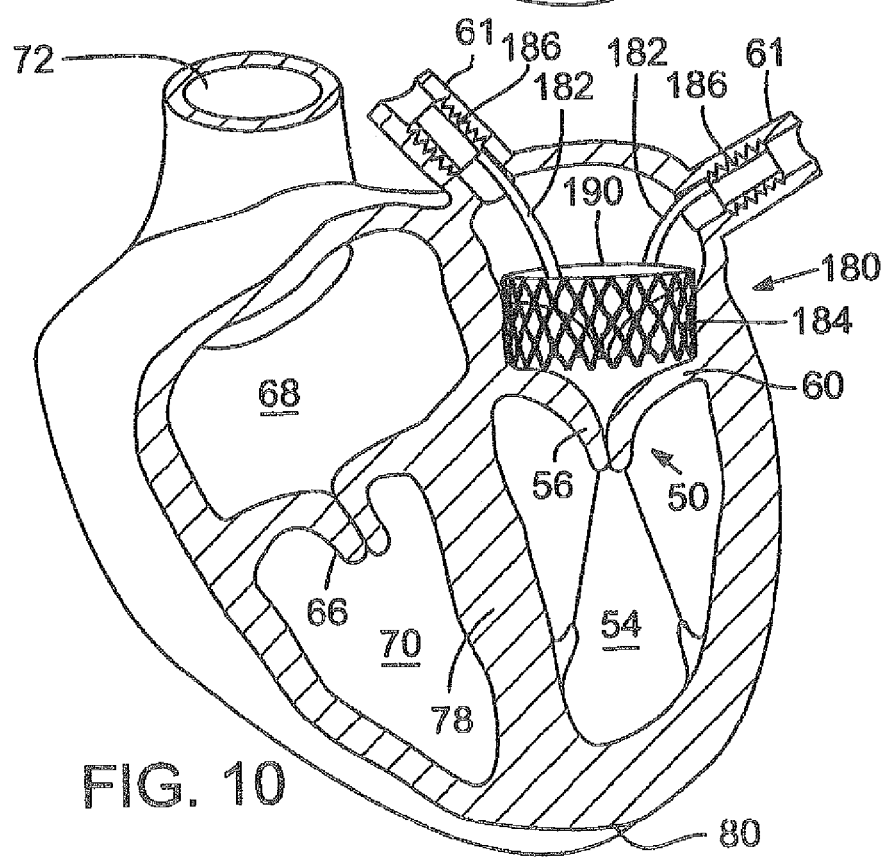
FIG. 10 is a cross-sectional view of a heart having another embodiment of the mitral valve assembly mounted in the left atrium with at least one anchoring arm extending into at least one pulmonary vein.

FIG. 10 shows a cross-sectional view of a heart with another embodiment of a prosthetic mitral-valve assembly 180 inserted into the atrium and positioned above the annulus 60 of the native mitral valve 50. This embodiment is similar to the embodiment of FIG. 8, except anchoring arms 182 are coupled to a stent frame 184 at one end and to one or more pulmonary veins 61 at an opposite end using threaded pulmonary vein screws 186. The threaded screws 186 are mounted into the pulmonary veins and secure the anchoring arms in place. The anchoring arms can therefore provide a downward pressure on the stent frame 184 in order to resist upward migration of the stent. The pulmonary vein screws 186 can be hollow to allow blood to flow therethrough. Additionally, the anchoring arms 182 can be made of a flexible metal (similar or identical to the stent) or polymer. Furthermore, although two anchoring arms are shown, any number of anchoring arms can be used (e.g., 1, 2, 3, or 4). As in the other embodiments, a biocompatible sheet 190 can be attached to the stent in order to prevent paravalvular leakage.

Figure 11:
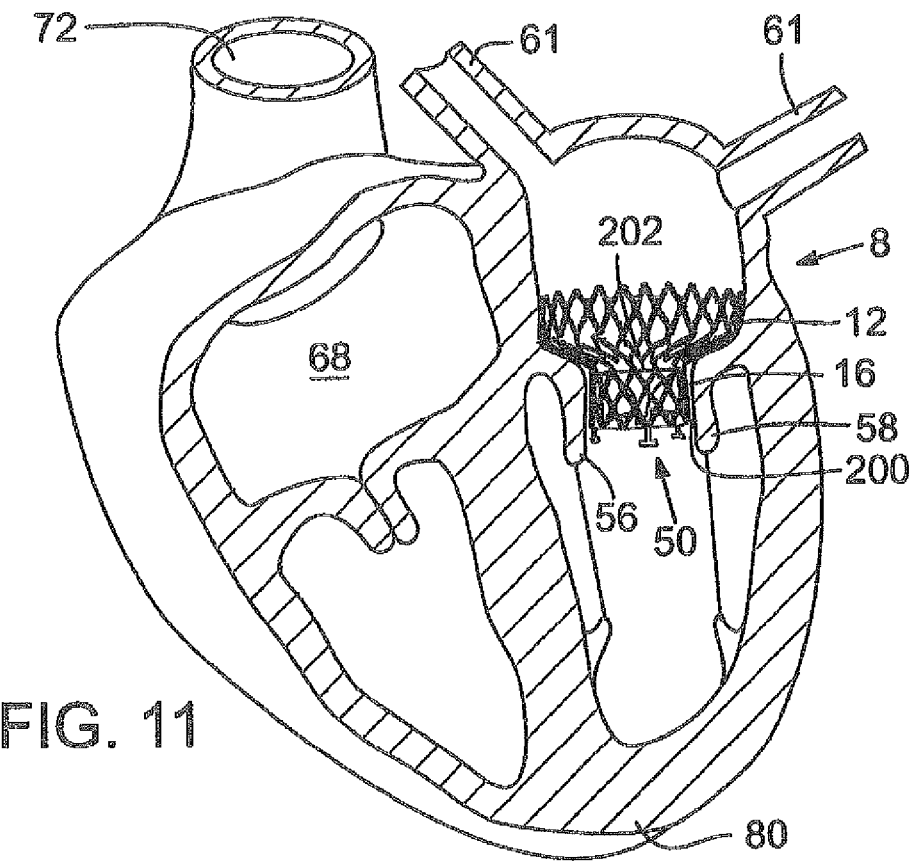
FIG. 11 is a cross-sectional view of a heart having the mitral valve assembly of FIG. 1 mounted in the left atrium with a lower portion of the mitral valve assembly positioned in the native mitral valve.

FIG. 11 shows a cross-sectional view of a heart with the prosthetic mitral-valve assembly 8 from FIG. 1 inserted into a patient's heart. As shown, the lower portion 16 can displace the native mitral valve leaflets 56, 58. The upper portion 12 allows for anchoring the stent 10 in the atrium. More particularly, the stent is secured in place using contact between the radially expanding upper portion 12 and the atrium walls. The lower portion 16 may or may not contact the native mitral valve leaflets 56, 58 as indicated by gaps 200 between the lower portion 16 and the mitral valve 50. A valve 202 is positioned in the lower portion 16 of the stent 10 so that the portion of the stent 10 for supporting the valve 202 is independent from the portion of the stent 10 for anchoring the stent in the heart. As in the other embodiments, a biocompatible sheet (not shown) can be attached to the stent in order to prevent paravalvular leakage.

Figure 12:
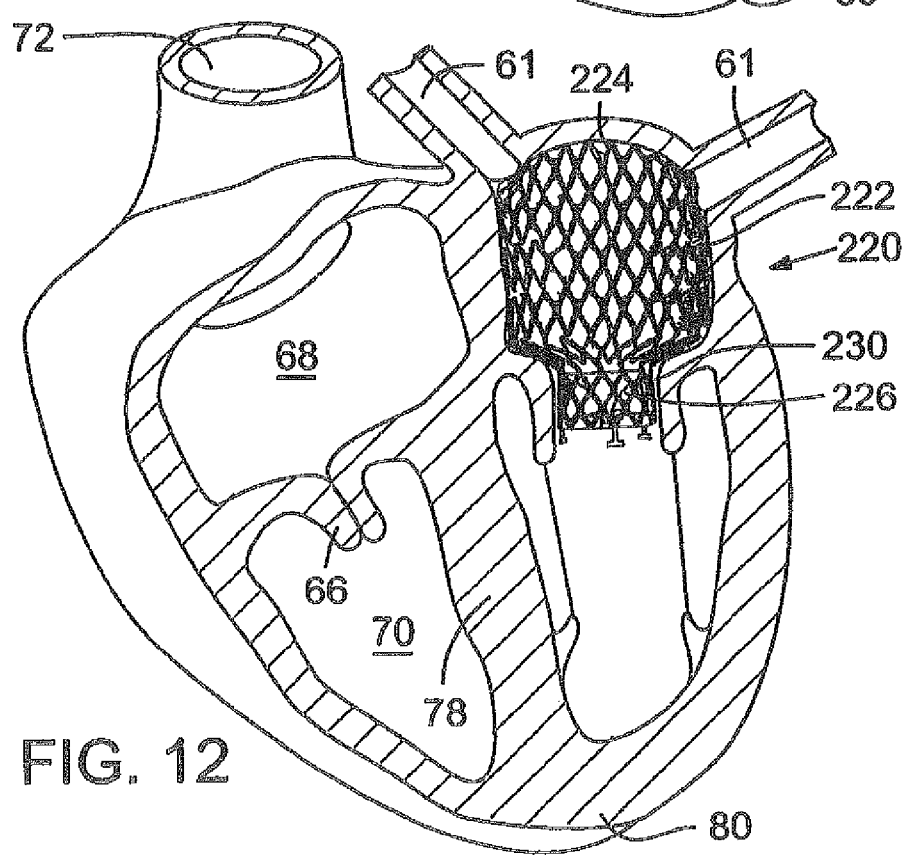
FIG. 12 is a cross-sectional view of a heart having another embodiment of the mitral valve assembly mounted in the left atrium with the mitral valve assembly extending to the roof of the atrium and with a lower portion of the mitral valve assembly positioned in the native mitral valve.

FIG. 12 shows a cross-sectional view of a heart with another embodiment of a prosthetic mitral-valve assembly 220 inserted into the atrium. In this embodiment, a stent 222 has a self-expanding frame similar to stents described above. The mitral valve assembly 222 has a dome-shaped upper portion 224 that can expand to fit the natural anatomical geometry of a roof of the atrium. As a result, the mitral valve assembly 220 can expand in two dimensions, such as a horizontal direction and a vertical direction, as indicated by the arrows. By expanding horizontally, the mitral-valve assembly uses side walls of the atrium to anchor the assembly. By expanding vertically, the assembly expands between the annulus of the mitral valve and the roof of the atrium in order to anchor the assembly in the atrium. Thus, the roof of the atrium can exert a downward pressure on the assembly in order to prevent upward migration. A valve 226 is positioned in the lower portion 230 of the stent so that the portion of the stent for supporting the valve 226 is independent from the portion of the stent for anchoring the stent in the heart. As in the other embodiments, a biocompatible sheet (not shown) is attached to the stent in order to prevent paravalvular leakage. However, the biocompatible sheet is desirably not be positioned so as to obstruct blood flow through the pulmonary veins.

Figure 13:
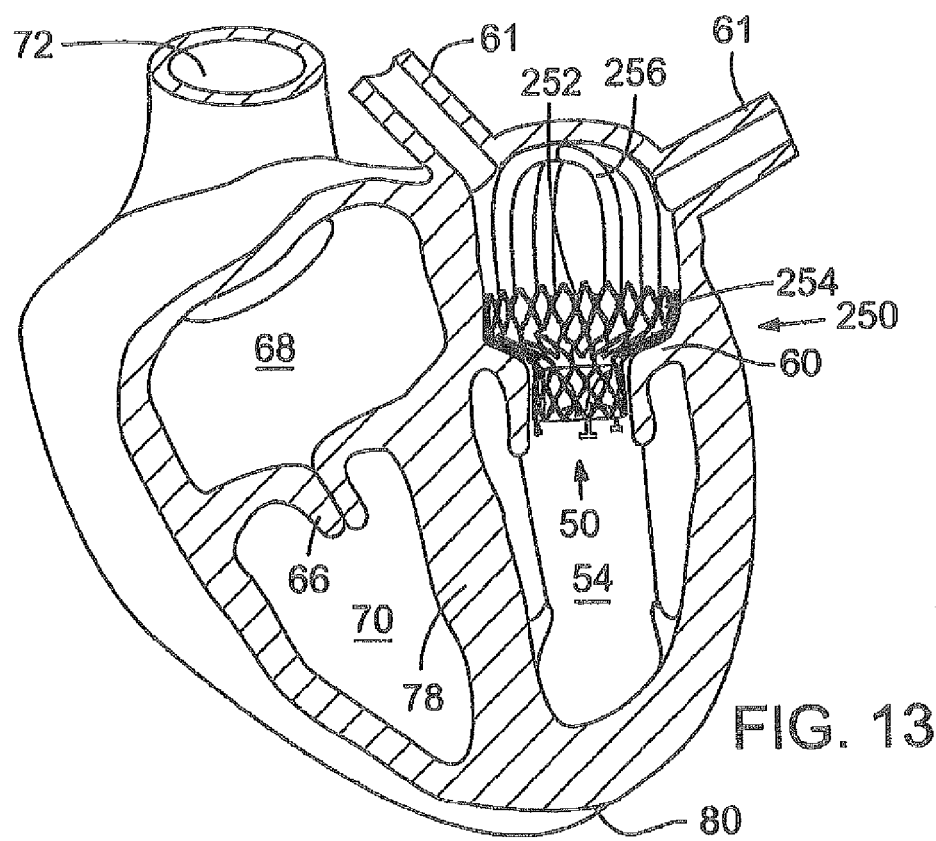
FIG. 13 is a cross-sectional view of a heart having another embodiment of the mitral valve assembly mounted in the left atrium with at least one anchoring arm extending to a roof of the atrium and with a lower portion of the mitral valve assembly positioned in the native mitral valve.

FIG. 13 shows a cross-sectional view of a heart with another embodiment of a prosthetic mitral-valve assembly 250 inserted into the atrium. As in the other embodiments, a biocompatible sheet 252 is attached to a stent frame 254 in order to prevent paravalvular leakage. Four anchoring arms 256 are coupled to the stent frame 254 so that they are equally spaced around the frame's circumference. The opposite ends of the anchoring arms 256 are coupled together adjacent the roof of the atrium to create an open-ended dome. The anchoring arms 256 allow the mitral valve assembly 250 to expand in two dimensions, such as a horizontal direction and a vertical direction. By expanding horizontally, the mitral-valve assembly uses side walls of the atrium to anchor the assembly. By expanding vertically, the assembly expands between the annulus of the mitral valve and the roof of the atrium in order to anchor the assembly in the atrium. Thus, the roof of the atrium can exert a downward pressure on the assembly in order to prevent upward migration. Although four anchoring arms are shown, any number of anchoring arms can be used (e.g., 1, 2, 3, 5, 6, etc.) Additionally, the anchoring arms 256 can be made of a flexible metal (similar or identical to the stent) or polymer.

Figure 14:
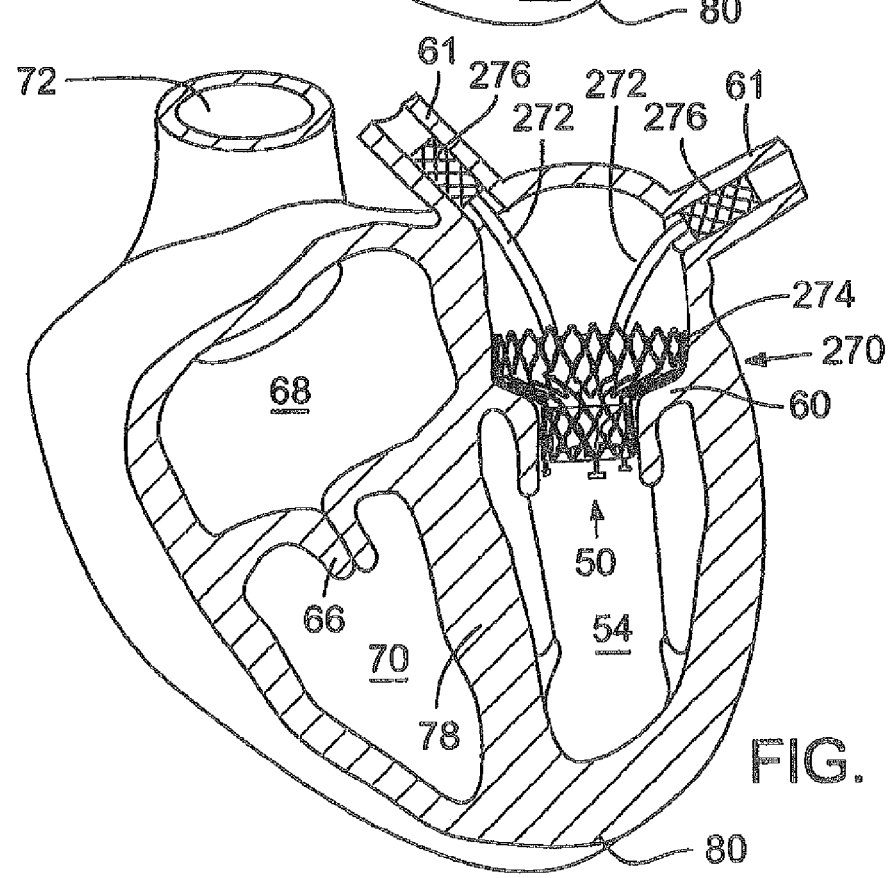
FIG. 14 is a cross-sectional view of a heart having another embodiment of the mitral valve assembly mounted in the left atrium with at least one anchoring arm extending into pulmonary veins and with a lower portion of the mitral valve assembly positioned in the native mitral valve.

FIG. 14 shows a cross-sectional view of a heart with another embodiment of a prosthetic mitral-valve assembly 270 inserted into the atrium and positioned above the annulus 60 of the native mitral valve 50. This embodiment also includes anchoring arms 272, similar to FIG. 13, except the anchoring arms 272 are coupled to a stent frame 274 at one end and to one or more pulmonary veins 61 at an opposite end. To couple the anchoring arms 272 to the pulmonary veins 61, pulmonary vein stents 276 are mounted into the pulmonary veins and are coupled to one end of the anchoring arms 272. The pulmonary vein stents 276 can be made from the same material as other stents described herein. Additionally, the anchoring arms 272 can be made of a flexible metal (similar or identical to the stent) or polymer. Furthermore, although two anchoring arms are shown, any number of anchoring arms can be used (e.g., 1, 2, 3, or 4). As in the other embodiments, a biocompatible sheet (not shown) can be attached to the stent in order to prevent paravalvular leakage.

Figure 15:
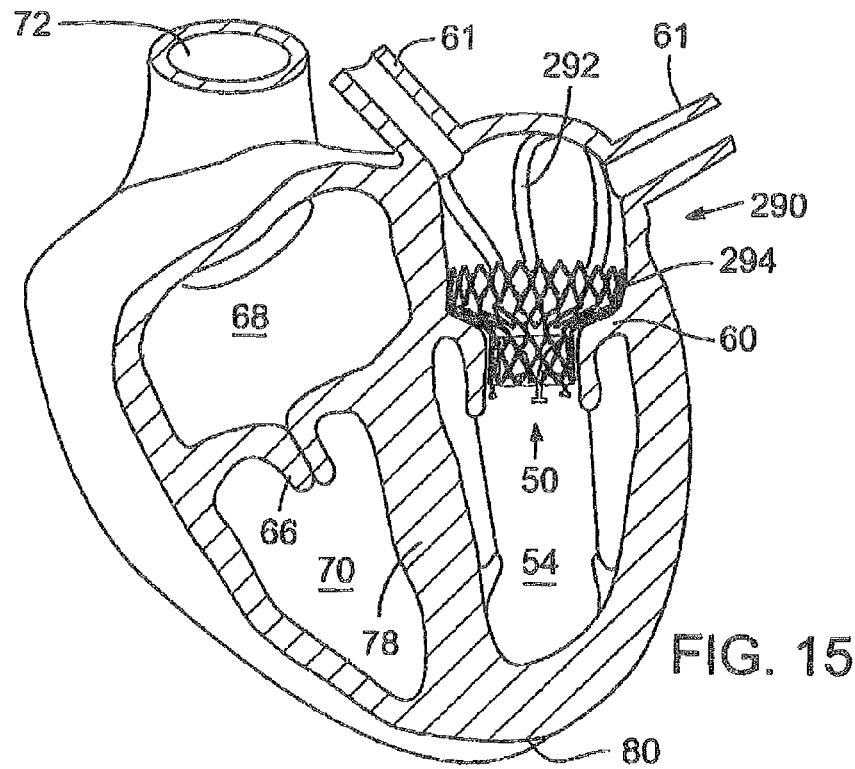
FIG. 15 is a cross-sectional view of a heart having another embodiment of the mitral valve assembly mounted in the left atrium with at least one anchoring arm extending to a roof of the atrium and with a lower portion of the mitral valve assembly positioned in the native mitral valve.

FIG. 15 shows a cross-sectional view of a heart with another embodiment of a prosthetic mitral-valve assembly 290 inserted into the atrium and positioned above the annulus 60 of the native mitral valve 50. The embodiment of FIG. 15 is similar to the embodiment of FIG. 13, but with one or more anchoring arms 292, each coupled at one end to a stent 294 and left uncoupled at an opposing end. The anchoring arms 292 can be made of a flexible metal (similar or identical to the stent) or polymer. Furthermore, although three anchoring arms are shown, any number of anchoring arms can be used (e.g., 1, 2, 3, or 4). The anchoring arms use the roof of the atrium to provide a pressure on the stent 294 in a direction of the mitral valve to prevent upward migration of the stent. As in the other embodiments, a biocompatible sheet (not shown) can be attached to the stent in order to prevent paravalvular leakage.

Figure 16:
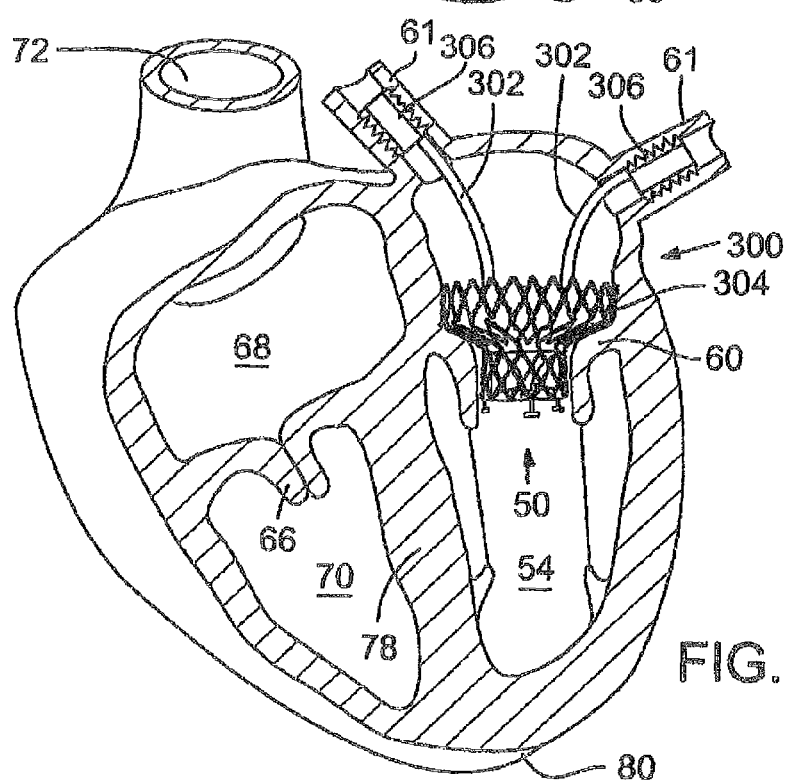
FIG. 16 is a cross-sectional view of a heart having another embodiment of the mitral valve assembly mounted in the left atrium with at least one anchoring arm extending into pulmonary veins and with a lower portion of the mitral valve assembly positioned in the native mitral valve.

FIG. 16 shows a cross-sectional view of a heart with another embodiment of a prosthetic mitral-valve assembly 300 inserted into the atrium and positioned above the annulus 60 of the native mitral valve 50. This embodiment is similar to the embodiment of FIG. 14, except anchoring arms 302 are coupled to a stent frame 304 at one end and to one or more pulmonary veins 61 at an opposite end using threaded pulmonary vein screws 306. The threaded screws 306 are mounted into the pulmonary veins and secure the anchoring arms in place. The anchoring arms can therefore provide a downward pressure on the stent frame 304 in order to resist upward migration of the stent. The pulmonary vein screws 306 can be hollow to allow blood to flow therethrough. Additionally, the anchoring arms 302 can be made of a flexible metal (similar or identical to the stent) or polymer. Furthermore, although two anchoring arms are shown, any number of anchoring arms can be used (e.g., 1, 2, 3, or 4). As in the other embodiments, a biocompatible sheet (not shown) can be attached to the stent in order to prevent paravalvular leakage.

Figure 17:
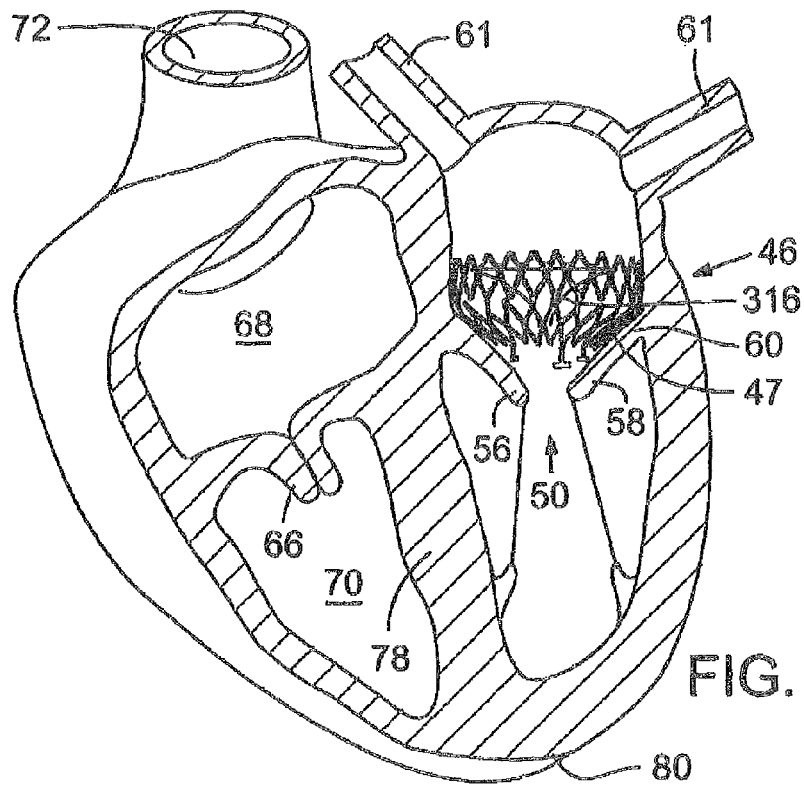
FIG. 17 is a cross-sectional view of a heart having the mitral valve assembly of FIG. 4 mounted in the left atrium.

FIG. 17 shows a cross-sectional view of a heart with the prosthetic mitral-valve assembly from FIG. 4 inserted into a patient's heart. As shown, the lower tapered portion 47 can partially displace the native mitral valve leaflets 56, 58. The upper portion allows for anchoring the stent in the atrium. More particularly, the stent is secured in place using contact between the radially expanding upper portion and the atrium walls. The lower portion 47 only partially engages the native mitral valve leaflets 56, 58, but is sized so as not to extend into the left ventricle. As in the other embodiments, a biocompatible sheet (not shown) can be attached to the stent in order to prevent paravalvular leakage.

Figure 18:
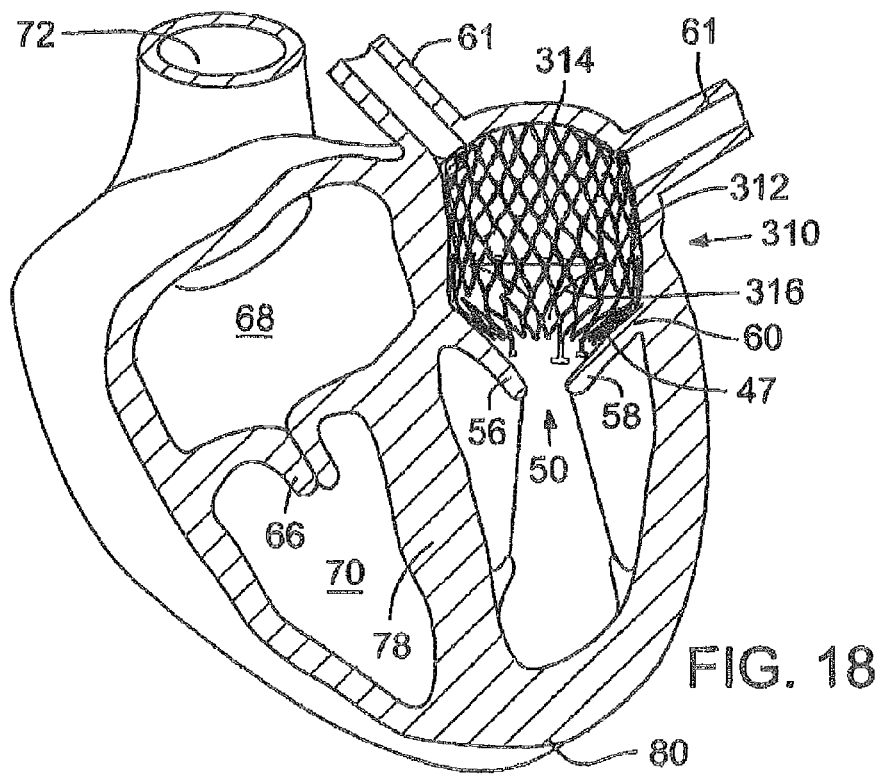
FIG. 18 is a cross-sectional view of a heart having another embodiment of the mitral valve assembly mounted in the left atrium with the mitral valve assembly extending to a roof of the atrium.

FIG. 18 shows a cross-sectional view of a heart with another embodiment of a prosthetic mitral-valve assembly 30 inserted into the atrium. In this embodiment, a stent has a self-expanding frame 312 similar to stents described above. The mitral valve assembly 310 has a dome-shaped upper portion 314 that can expand to fit the natural anatomical geometry of a roof of the atrium. As a result, the mitral valve assembly can expand in two dimensions, such as a horizontal direction and a vertical direction. By expanding horizontally, the mitral-valve assembly uses side walls of the atrium to anchor the assembly. By expanding vertically, the assembly expands between the annulus of the mitral valve and the roof of the atrium in order to anchor the assembly in the atrium. Thus, the roof of the atrium can exert a downward pressure on the assembly in order to prevent upward migration. A valve 316 is positioned in the lower portion of the stent so that the portion of the stent for supporting the valve can be independent from the portion of the stent for anchoring the assembly in the heart. As in the other embodiments, a biocompatible sheet (not shown) can be attached to the stent in order to prevent paravalvular leakage. However, the sheet should be sized so as not to obstruct blood flow in the pulmonary veins.

Figure 19:
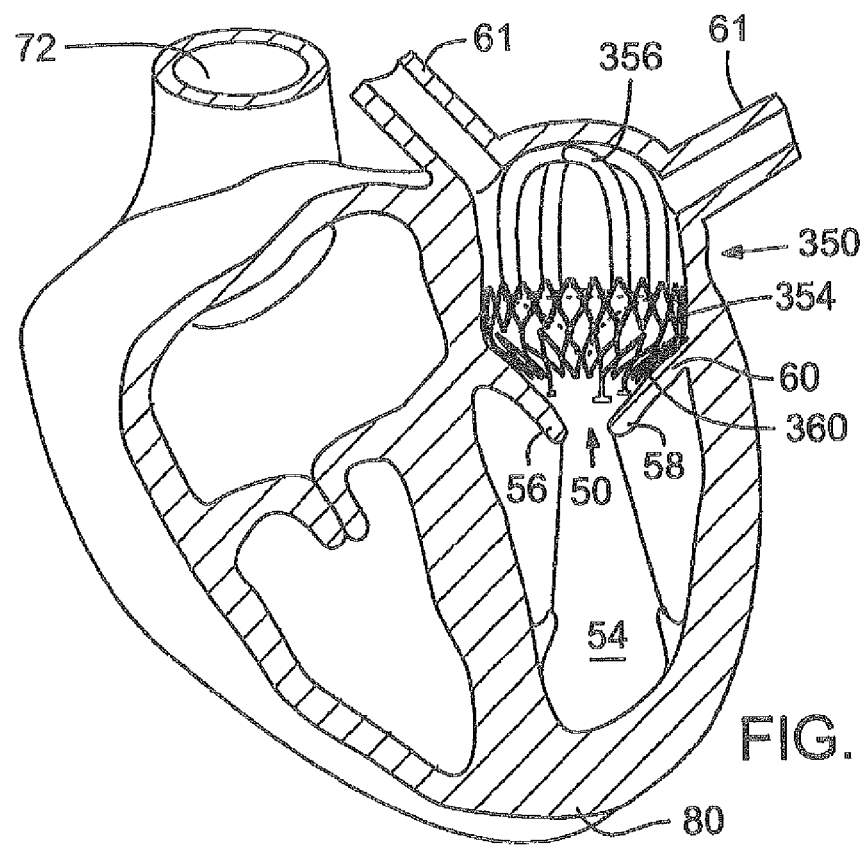
FIG. 19 is a cross-sectional view of a heart having another embodiment of the mitral valve assembly mounted in the left atrium with at least one anchoring arm extending to a roof of the atrium and with a lower portion of the mitral valve assembly partially extending into the native mitral valve.

FIG. 19 shows a cross-sectional view of a heart with another embodiment of a prosthetic mitral-valve assembly 350 inserted into the atrium. This embodiment has characteristics of the mitral valve assembly of FIG. 4, but with additional atrial anchoring. As in the other embodiments, a biocompatible sheet (not shown) can be attached to a stent frame 354 in order to prevent paravalvular leakage. Four anchoring arms 356 are coupled to the stent frame 354 so that they are equally spaced around the frame's circumference. The opposite ends of the anchoring arms 356 are coupled together adjacent the roof of the atrium to create an open-ended dome. The anchoring arms 356 allow the mitral valve assembly 350 to expand in two dimensions, such as a horizontal direction and a vertical direction. By expanding horizontally, the mitral-valve assembly uses side walls of the atrium to anchor the assembly. By expanding vertically, the assembly expands between the annulus of the mitral valve and the roof of the atrium in order to anchor the assembly in the atrium. Thus, the roof of the atrium can exert a downward pressure on the assembly in order to prevent upward migration. Although four anchoring arms are shown, any number of anchoring arms can be used (e.g., 1, 2, 3, 5, 6, etc.) Additionally, the anchoring arms 356 can be made of a flexible metal (similar or identical to the stent) or polymer. A lower tapered portion 360 of the mitral valve assembly 350 partially extends into the native mitral valve, but can remain distant enough from the left ventricle so as not to damage the chordae tendineae.

Figure 20:
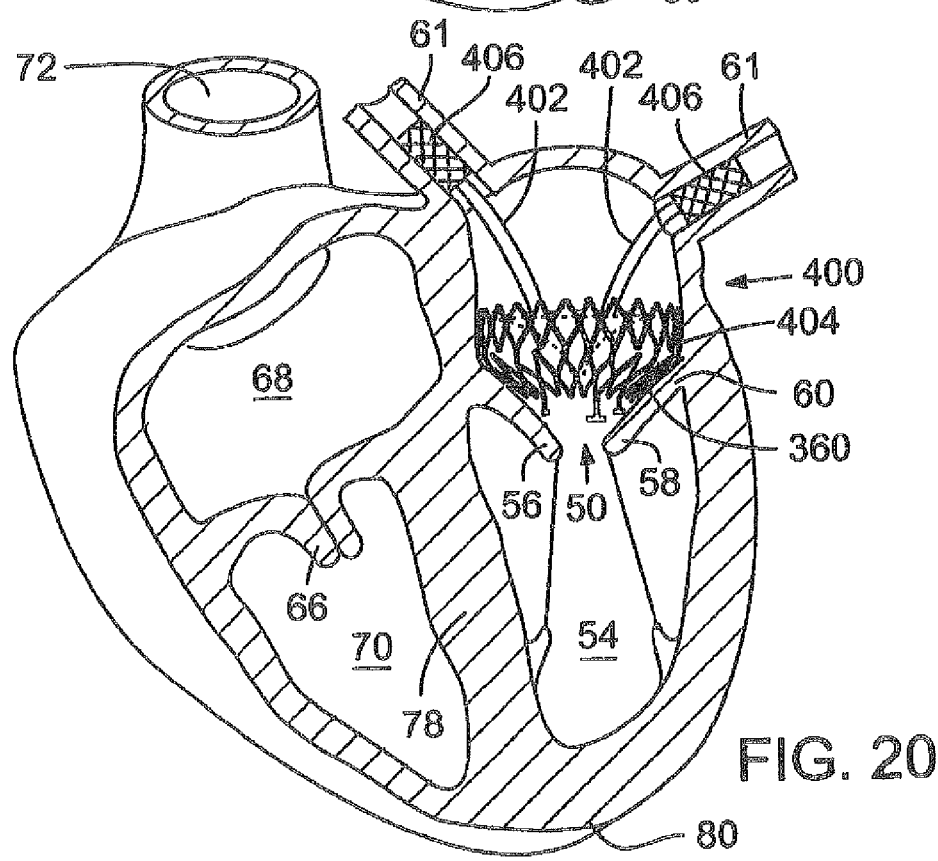
FIG. 20 is a cross-sectional view of a heart having another embodiment of the mitral valve assembly mounted in the left atrium with at least one anchoring arm extending into pulmonary veins and with a lower portion of the mitral valve assembly partially extending into the native mitral valve.

FIG. 20 shows a cross-sectional view of a heart with another embodiment of a prosthetic mitral-valve assembly 400 inserted into the atrium and a majority thereof positioned above the annulus 60 of the native mitral valve 50. This embodiment also includes anchoring arms 402, similar to FIG. 8 with the anchoring arms 402 coupled to a stent frame 404 at one end and to one or more pulmonary veins 61 at an opposite end. To couple the anchoring arms 402 to the pulmonary veins 61, pulmonary vein stents 406 are mounted into the pulmonary veins and are coupled to one end of the anchoring arms 402. The pulmonary vein stents 406 can be made from the same material as other stents described herein. Additionally, the anchoring arms 402 can be made of a flexible metal (similar or identical to the stent) or polymer. Furthermore, although two anchoring arms are shown, any number of anchoring arms can be used (e.g., 1, 2, 3, or 4). As in the other embodiments, a biocompatible sheet (not shown) can be attached to the stent in order to prevent paravalvular leakage.

Figure 21:
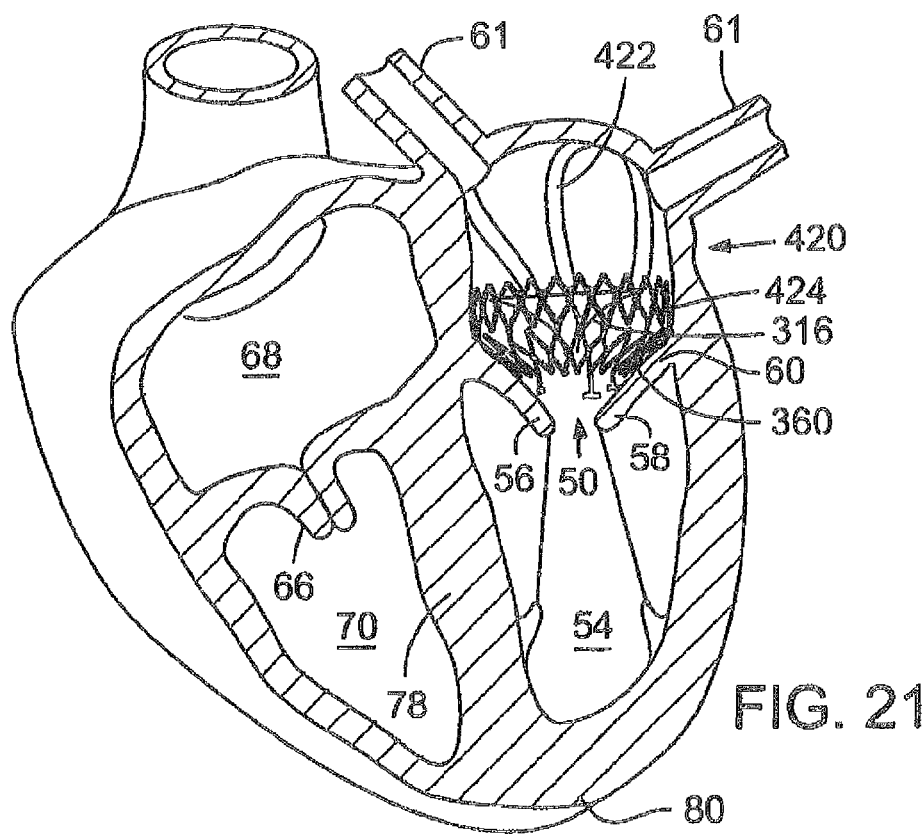
FIG. 21 is a cross-sectional view of a heart having another embodiment of the mitral valve assembly mounted in the left atrium with at least one anchoring arm extending to a roof of the atrium and with a lower portion of the mitral valve assembly partially extending into the native mitral valve.

FIG. 21 shows a cross-sectional view of a heart with another embodiment of a prosthetic mitral-valve assembly 420 inserted into the atrium and positioned above the annulus 60 of the native mitral valve 50. The embodiment of FIG. 21 is similar to the embodiment of FIG. 15, with one or more anchoring arms 422, each coupled at one end to a stent 424 and left uncoupled at an opposing end. The anchoring arms 422 can be made of a flexible metal (similar or identical to the stent) or polymer. Furthermore, although three anchoring arms are shown, any number of anchoring arms can be used (e.g., 1, 2, 3, or 4). The anchoring arms use the roof of the atrium to provide a pressure on the stent 424 in a direction of the mitral valve to prevent upward migration of the stent. As in the other embodiments, a biocompatible sheet (not shown) can be attached to the stent in order to prevent paravalvular leakage.

Figure 22:
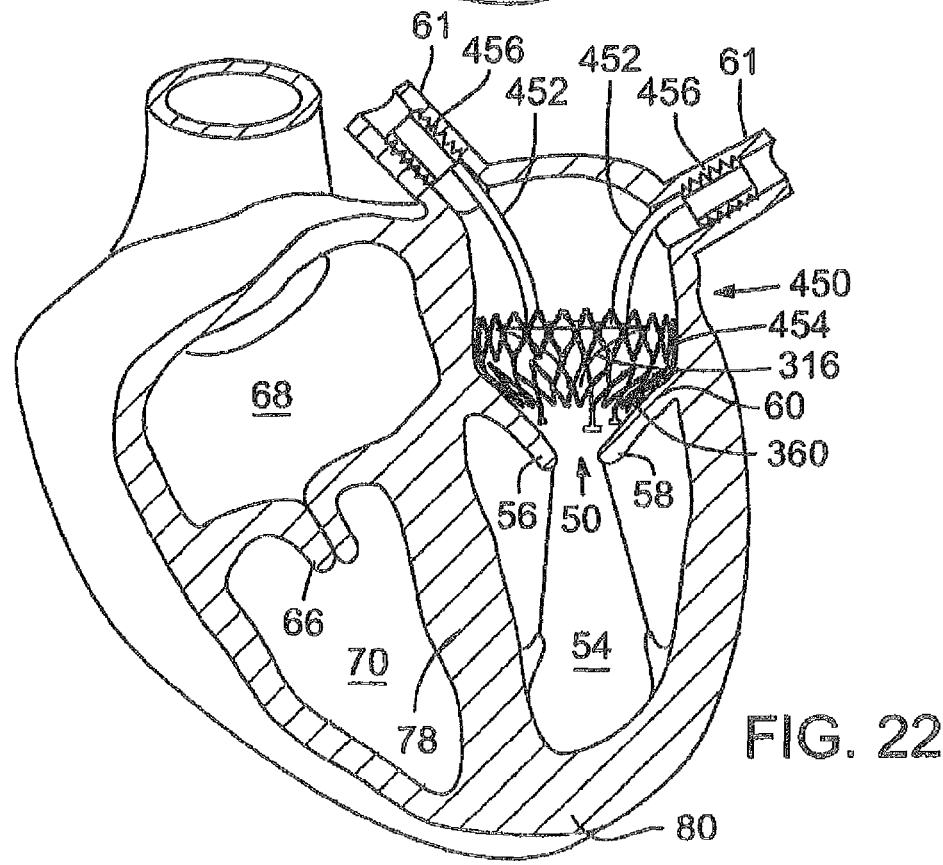
FIG. 22 is a cross-sectional view of a heart having another embodiment of the mitral valve assembly mounted in the left atrium with at least one anchoring arm extending into pulmonary veins and with a lower portion of the mitral valve assembly partially extending into the native mitral valve.

FIG. 22 shows a cross-sectional view of a heart with another embodiment of a prosthetic mitral-valve assembly 450 inserted into the atrium and positioned above the annulus 60 of the native mitral valve 50. This embodiment is similar to the embodiment of FIG. 16 with anchoring arms 452 coupled to a stent frame 454 at one end and to one or more pulmonary veins 61 at an opposite end using threaded pulmonary vein screws 456. The threaded screws 456 are mounted into the pulmonary veins and secure the anchoring arms in place. The anchoring arms can therefore provide a downward pressure on the stent frame 454 in order to resist upward migration of the stent. The pulmonary vein screws 456 can be hollow to allow blood to flow therethrough. Additionally, the anchoring arms 452 can be made of a flexible metal (similar or identical to the stent) or polymer. Furthermore, although two anchoring arms are shown, any number of anchoring arms can be used (e.g., 1, 2, 3, or 4). As in the other embodiments, a biocompatible sheet (not shown) can be attached to the stent in order to prevent paravalvular leakage.

Many of the embodiments described herein show one or more optional extension arms 500 that are used to assist in the delivery of the disclosed embodiments to the heart of a patient, as further described below. The extension arms 500 are generally shown as T-shaped extensions, but can be circular or other geometric shapes. Likewise, the extension arms 500 can be made of metal or a suture material.

FIGS. 23A-23E illustrate a delivery apparatus 700. The delivery apparatus 700 comprises an outer catheter shaft 702 and an inner catheter shaft 704 extending through the outer shaft. The distal end portion of the outer shaft 702 comprises a sheath that extends over a prosthetic, self-expanding stented valve 706 (shown schematically) and retains it in a compressed state during delivery through the patient's vasculature. The distal end portion of the inner shaft 704 is shaped to cooperate with one or more mating extension arms, or posts, 708 that extend from the stent of the valve 706 to form a releasable connection between the valve and the delivery apparatus. For example, in the illustrated embodiment each post 708 comprises a straight portion terminating at a circular ring portion and the distal end portion of the shaft 704 has correspondingly shaped recesses 710 that receive respective posts 708. Each recess 710 can include a radially extending projection 712 that is shaped to extend into an opening 714 in a respective post 708. As best shown in FIG. 23B, each recess 710 and projection 712 can be sized to provide a small gap between the surfaces of the post 708 and the adjacent surfaces within the recess to facilitate insertion and removal of the post from the recess in the radial direction (i.e., perpendicular to the axis of the shaft 704).

When the valve 706 is loaded into the delivery apparatus 700, as depicted in FIG. 23A, such that each post 708 of the valve is disposed in a recess 710, the valve is retained against axial movement relative to the shaft 704 (in the proximal and distal directions) by virtue of the shape of the posts and the corresponding recesses. Referring to FIG. 23D, as the outer shaft 702 is retracted to deploy the valve 706, the valve is allowed to expand but is retained against "jumping" from the distal end of the sheath by the connection formed by the posts and the corresponding recesses for controlled delivery of the valve. At this stage the partially deployed valve is still retained by the shaft 704 and can be retracted back into the outer sheath 702 by retracting the shaft 704 relative to the outer sheath 702. Referring to FIG. 23E, when the outer sheath is retracted in the proximal direction past the posts 708, the expansion force of the valve stent causes the posts to expand radially outwardly from the recesses 710, thereby fully releasing the valve from the shaft 704.

While three posts 708 and corresponding recesses 710 are shown in the illustrated embodiment, any number of posts and recesses can be used. Furthermore, the posts and recesses can have various other shapes, such as square, oval, rectangular, triangular, or various combinations thereof. The posts can be formed from the same material that is used to form the valve stent (e.g., stainless steel or Nitinol). Alternatively, the posts can be loops formed from less rigid material, such as suture material. The loops are secured to the valve stent and are sized to be received in the recesses 710.

FIGS. 24A-24D illustrate a delivery apparatus 800 that is similar to the delivery apparatus shown in FIGS. 23A-23E. The delivery apparatus 800 includes a handle portion 802 having a rotatable knob 804, an outer catheter shaft 806 extending from the handle portion 802, and an inner catheter shaft 808 extending from the handle portion and through the outer catheter shaft 806. The distal end of the inner catheter shaft 808 includes an end piece 810 that is formed with an annular recess 812 and a plurality of axially extending, angularly spaced recesses 814. The recesses 812, 814 are sized and shaped to receive T-shaped posts 816 extending from the stent of a valve (not shown in FIGS. 24A-24D). Each post 816 has an axially extending portion 816*a* that is received in a corresponding recess 814 and a transverse end portion 816*b* that is received in the annular recess 812. The outer shaft 806 includes a sheath 818 that is sized and shaped to extend over the end piece 812 and the valve during delivery of the valve.

The outer shaft 806 is operatively connected to the knob 804 to effect longitudinal movement of the outer shaft 806 and the sheath 818 relative to the inner shaft 808 upon rotation of the knob 804. In use, the valve is mounted for delivery by placing the posts 816 of the valve in the recesses 812, 814 and moving the sheath distally to extend over the valve to maintain the valve in a compressed state. At or near the target site for implanting the valve, the knob 804 is rotated to retract the sheath 818 relative to the valve. As the sheath is retracted to deploy the valve, the valve is allowed to expand but is retained against "jumping" from the distal end of the sheath by the connection formed by the posts and the corresponding recesses for controlled delivery of the valve. At this stage the partially deployed valve is still retained by the end piece 810 and can be retracted back into the sheath by moving the shaft 806 distally relative to the valve. When the sheath is retracted in the proximal direction past the posts 816, the expansion force of the valve stent causes the posts to expand radially outwardly from the recesses 812, 814, thereby fully releasing the valve from the end piece 810.

Figure 25:
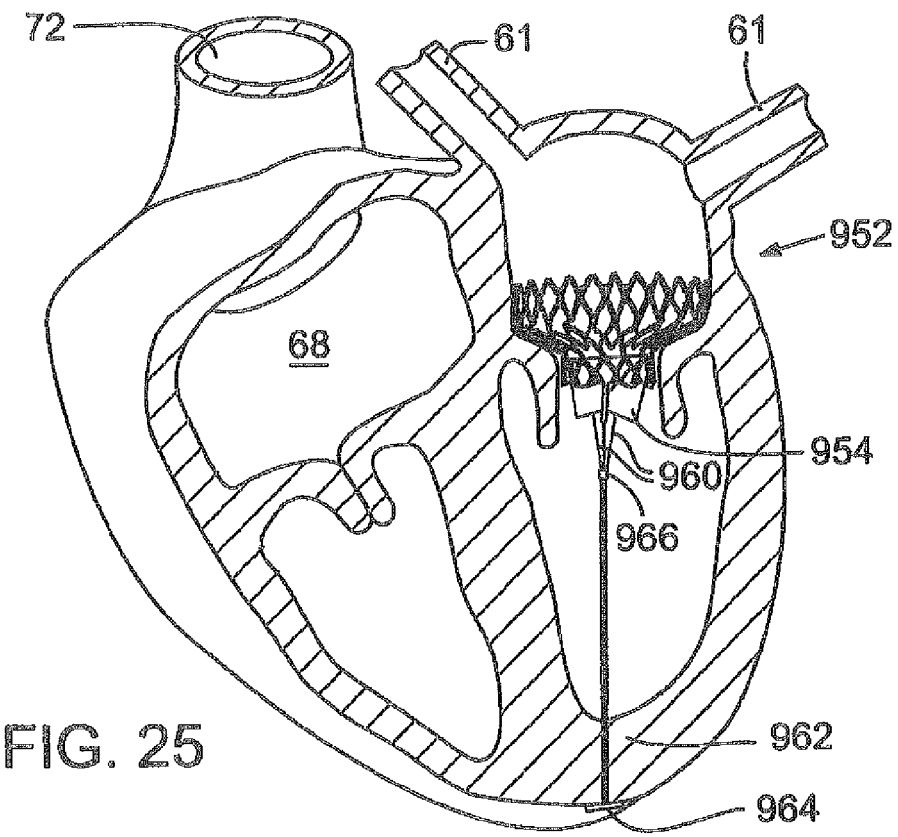
FIG. 25 is a perspective view of an embodiment of a prosthetic valve assembly having tensioning members coupled to prosthetic leaflets of the valve to simulate chordae tendineae.

FIG. 25 shows an embodiment comprising a prosthetic mitral valve assembly 952 having leaflets 954. Each leaflet 954 can be connected to a respective tension member 960, the lower ends of which can be connected at a suitable location on the heart. For example, the lower end portions of tension members 960 can extend through the apex 962 and can be secured in placed at a common location outside the heart. Tension members may be attached to or through the papillary muscles. The lower ends of tension members can be connected to an enlarged head portion, or anchor, 964, which secures the tension members to the apex. Tension members 960 can extend through a tensioning block 966. The tensioning block 966 can be configured to slide upwardly and downwardly relative to tension members 960 to adjust the tension in the tensioning members. For example, sliding the tensioning block 966 upwardly is effective to draw the upper portions of the tension members closer together, thereby increasing the tension in the tension members. The tensioning block 966 desirably is configured to be retained in place along the length of the tension members, such as by crimping the tensioning block against the tension members, once the desired tension is achieved. The tension members can be made of any suitable biocompatible material, such as traditional suture material, GORE-TEX®, or an elastomeric material, such as polyurethane. The tension members 960 further assist in securing the valve assembly in place by resisting upward movement of the valve assembly and prevent the leaflets 954 from everting so as to minimize or prevent regurgitation through the valve assembly. As such, the tethering de-stresses the moveable leaflets.

Figure 26:
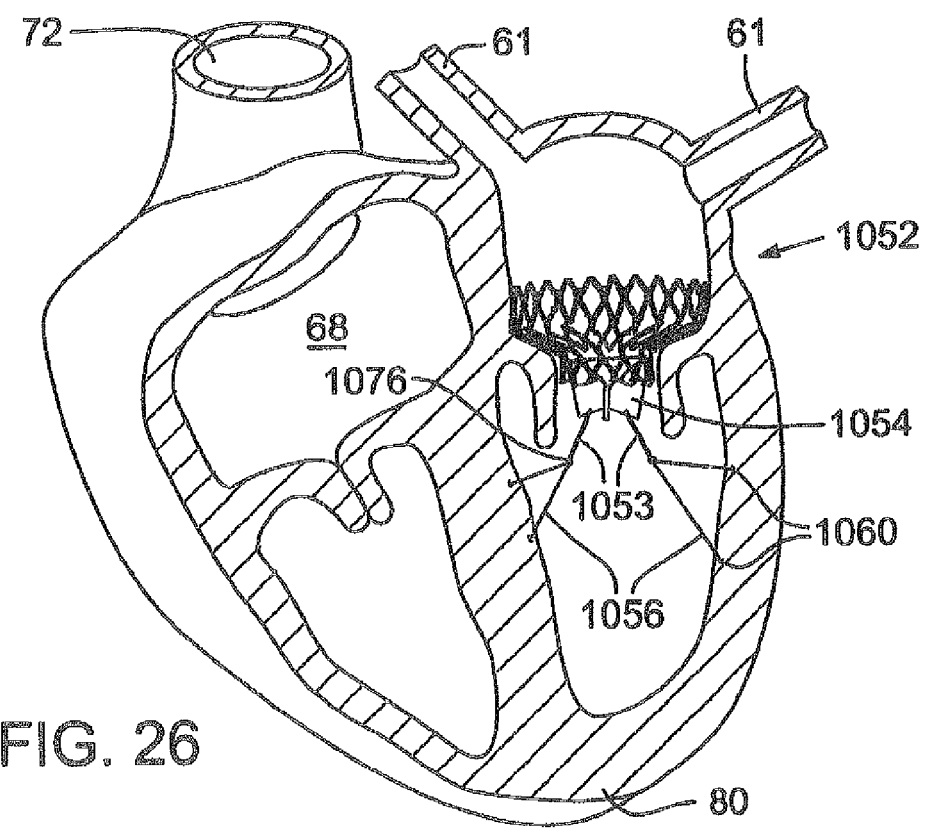
FIG. 26 is a perspective view of a prosthetic valve assembly having tensioning members, according to another embodiment.

FIG. 26 shows another embodiment of a mitral valve assembly 1052 having prosthetic chordae tendineae. The prosthetic chordae tendineae comprise first and second tension members 1053 connected to a respective leaflet 1054 of the valve assembly. As shown, the lower end portions 1056 of each tension member 1053 can be connected at spaced apart locations to the inner walls of the left ventricle, using, for example, anchor members 1060. A slidable tensioning block 1076 can be placed over each tension member 1053 for adjusting the tension in the corresponding tension member. In certain embodiments, each tension member 1053 can comprise a suture line that extends through a corresponding leaflet 1054 and has its opposite ends secured to the ventricle walls using anchor members 1060.

In particular embodiments, the anchor member 1060 can have a plurality of prongs that can grab, penetrate, and/or engage surrounding tissue to secure the device in place. The prongs of the anchor member 1060 can be formed from a shape memory material to allow the anchor member to be inserted into the heart in a radially compressed state (e.g., via an introducer) and expanded when deployed inside the heart. The anchor member can be formed to have an expanded configuration that conforms to the contours of the particular surface area of the heart where the anchor member is to be deployed, such as described in co-pending application Ser. No. 11/750,272, published as US 2007-0270943 A1, which is incorporated herein by reference. Further details of the structure and use of the anchor member are also disclosed in co-pending application Ser. No. 11/695,583 to Rowe, filed Apr. 2, 2007, which is incorporated herein by reference.

Alternative attachment locations in the heart are possible, such as attachment to the papillary muscle (not shown). In addition, various attachment mechanisms can be used to attach tension members to the heart, such as a barbed or screw-type anchor member. Moreover, any desired number of tension members can be attached to each leaflet (e.g., 1, 2, 3 . . . etc.). Further, it should be understood that tension members can be used on any of the embodiments disclosed herein.

FIGS. 25-26 show the use of tension members that can mimic the function of chordae. The tethers can have several functions including preventing the valve from migrating into the left atrium, distressing the leaflets by preventing eversion, and preserving ventricular function by maintaining the shape of the left ventricle. In particular, the left ventricle can lose its shape over time as the natural chordae become stretched or break. The artificial chordae can help to maintain the shape. Although FIGS. 25 and 26 show a tricuspid valve, a bicuspid valve can be used instead.

Figure 27:
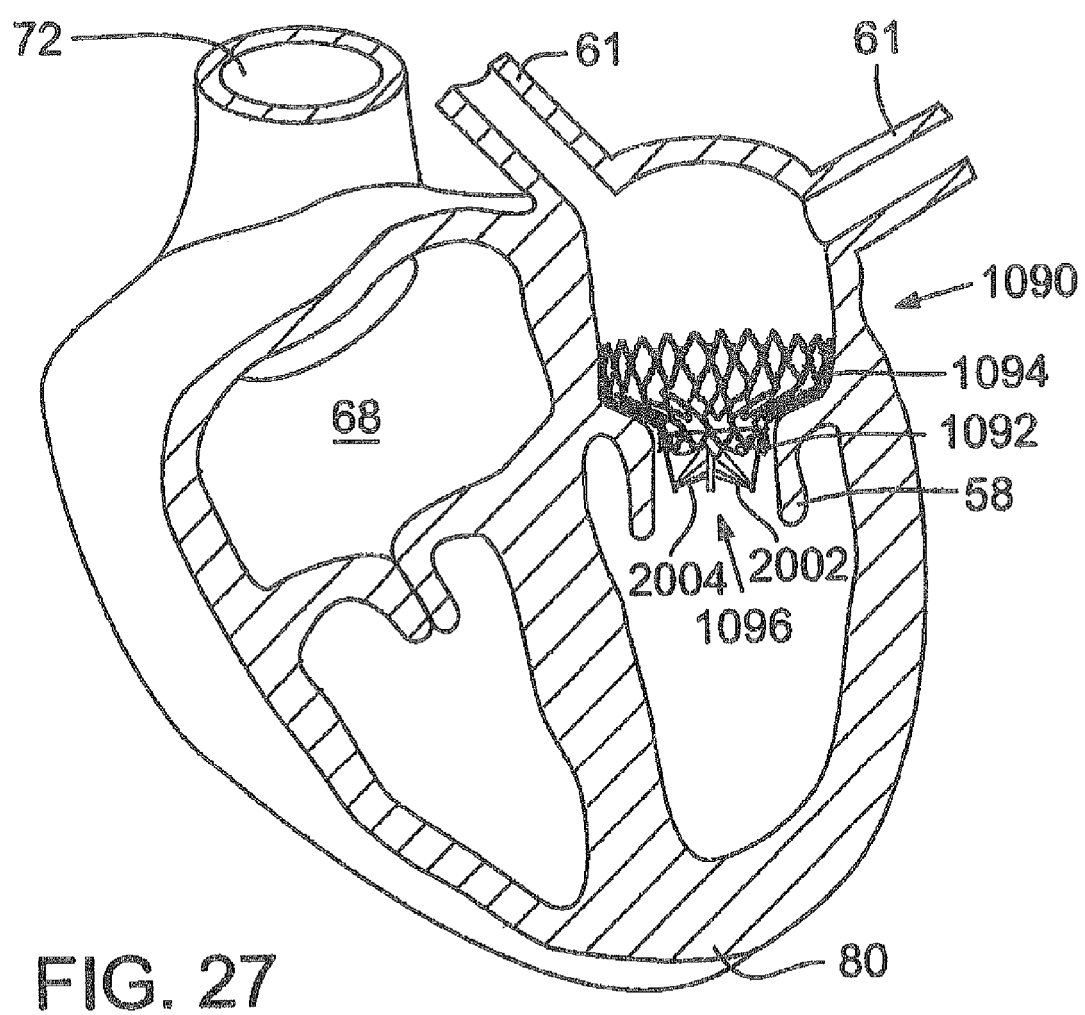
FIG. 27 is a perspective view of a prosthetic valve assembly having tensioning members, according to another embodiment.

FIG. 27 shows another embodiment of a mitral valve assembly 1090 including a valve 1092 and a stent 1094 (shown partially cut-away to expose a portion of the valve). Tension members, shown generally at 1096, can be connected between leaflets of the valve 1092 and the stent itself. Only two leaflets are shown, but additional tension members can be used for a third leaflet in a tricuspid valve. In the illustrated embodiment, the tension members 1096 can include groups 2002, 2004 of three tension members each. The three tension members 1096 of group 2002 can be attached, at one end, to one of the leaflets at spaced intervals and converge to attach at an opposite end to a bottom of the stent 1094. Group 2004 can be similarly connected between another of the leaflets and the bottom of the stent 1094. The tension members 1096 can be made of any suitable biocompatible material, such as traditional suture material, GORE-TEX®, or an elastomeric material, such as polyurethane. The tension members can prevent the leaflets from everting so as to minimize or prevent regurgitation through the valve assembly. As such, the tension members de-stress the moveable portions of the leaflets when the leaflets close during systole without the need to connect the tension members to the inner or outer wall of the heart.

Although groups of three tension members are illustrated, other connection schemes can be used. For example, each group can include any desired number of tension members (e.g., 1, 2, 3, . . . etc.). Additionally, the tension members can connect to any portion of the stent and at spaced intervals, if desired. Likewise, the tension members can connect to the leaflets at a point of convergence, rather than at spaced intervals. Further, the tension members can be used on bicuspid or tricuspid valves. Still further, it should be understood that tension members extending between the stent and the leaflets can be used on any of the embodiments disclosed herein.

One skilled in the art will recognize that the tethering shown in FIGS. 25-27 can be used with any of the embodiments described herein.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

We claim:

1. A method of implanting a prosthetic mitral valve assembly, comprising:
    placing a suture at an apex of a heart into which the mitral valve is to be implanted;
    inserting a delivery catheter through the apex of the heart at the suture location, the delivery catheter including the prosthetic mitral valve assembly in a collapsed state, the prosthetic mitral valve assembly including a first pulmonary vein stent comprising a self-expanding metal lattice, a second pulmonary vein stent comprising a self-expanding metal lattice, a self-expanding mitral valve stent, a first anchoring arm coupling the first pulmonary vein stent and the mitral valve stent, and a second anchoring arm coupled between the second pulmonary vein stent and the mitral valve stent;
    positioning the first pulmonary vein stent in a first pulmonary vein, the first pulmonary vein stent being coupled to a first end of the first anchoring arm;
    advancing the first pulmonary vein stent from the delivery catheter;
    radially expanding the first pulmonary vein stent to anchor it entirely within the first pulmonary vein;
    positioning the second pulmonary vein stent in a second pulmonary vein, the second pulmonary vein stent coupled to a first end of the second anchoring arm;
    advancing the second pulmonary vein stent from the delivery catheter;
    radially expanding the second pulmonary vein stent, thereby anchoring the second pulmonary vein stent entirely within the second pulmonary vein;
    after expanding the first pulmonary vein stent and the second pulmonary vein stent, positioning the mitral valve stent coupled to a second end of the first anchoring arm and a second end of the second anchoring arm in a native mitral valve;
    advancing an inner catheter shaft of the delivery catheter relative to an outer catheter shaft thereof, thereby advancing the mitral valve stent from the delivery catheter;
    releasing extension arms extending from a lower end of the mitral valve stent from engagement with the inner catheter shaft;
    radially expanding the mitral valve stent to contact an upper portion thereof against a wall of the left atrium, to anchor prongs extending from and integral with a tapered middle portion thereof against the wall of the left atrium, and to contact a lower portion thereof within an annulus of the native mitral valve, a circumference of the lower portion less than a circumference of the upper portion, the mitral valve stent including a pericardium sheet coupled to an inner surface thereof and a prosthetic valve comprising a plurality of pericardium leaflets disposed in the lower portion thereof, with the first pulmonary vein stent and the second pulmonary vein stent further securing the mitral valve stent in place through coupling of the first anchoring arm and the second anchoring arm between the first and second pulmonary vein stents and the mitral valve stent; and
    removing the delivery catheter through the apex of the heart and closing the suture.

2. The method of claim 1, wherein the mitral valve stent is radially-expandable and wherein positioning the mitral valve stent includes placing the mitral valve stent above an annulus of the native mitral valve.

3. The method of claim 1, further including coupling tension members to the pericardium leaflets for preventing the pericardium leaflets from everting.

4. The method of claim 3, wherein the pericardium leaflets are coupled at a first end of the tension members and further including coupling an opposite end of the tension members to the stent or to a patient's heart.

5. The method of claim 1, further including coupling a tether to the mitral valve stent on one end thereof, the tether being configured to couple the mitral valve stent to a portion of the heart remote from the mitral valve stent.

6. The method of claim 1, wherein the first and second anchoring arms are made of a flexible metal or polymer.

7. The method of claim 1, wherein the first and second pulmonary vein stents resist upward migration of the mitral valve stent towards the atrium.

8. A method of implanting a prosthetic mitral valve, comprising:

inserting a prosthetic mitral valve assembly in a collapsed state through an apex of a heart using a delivery catheter, the prosthetic mitral valve assembly including a pulmonary vein stent, a mitral valve stent, and an anchoring arm coupled between the pulmonary vein stent and the mitral valve stent;

radially expanding the pulmonary valve stent entirely within a pulmonary vein;

radially expanding the mitral valve stent in a native mitral valve so that the anchoring arm extends between the pulmonary valve stent and the mitral valve stent, with an upper portion of the mitral valve stent contacting a wall of the left atrium, and a lower portion anchored in an annulus of the native mitral valve, a circumference of the lower portion less than a circumference of the upper portion, a tapered middle portion coupling the upper portion and the lower portion, a prosthetic valve comprising a plurality of pericardium leaflets disposed in the lower portion; and removing the delivery catheter through the apex of the heart and closing a suture in the apex.

9. The method of claim 8, wherein the mitral valve stent is radially-expandable and wherein positioning the mitral valve stent includes placing the mitral valve stent above an annulus of the native mitral valve.

10. The method of claim 8, further including coupling tension members to the pericardium leaflets for preventing the pericardium leaflets from everting.

11. The method of claim 10, wherein the pericardium leaflets are coupled at a first end of the tension members and further including coupling an opposite end of the tension members to the mitral valve stent or to a patient's heart.

12. The method of claim 8, further including coupling a tether to the mitral valve stent on one end thereof, the tether being configured to couple the mitral valve stent to a portion of the heart remote from the mitral valve stent.

13. The method of claim 8, wherein the mitral valve stent includes prongs extending outwardly therefrom that are integral therewith.

14. The method of claim 8, wherein the anchoring arm is made of a flexible metal or polymer.

15. The method of claim 8, wherein the pulmonary vein stent resists upward migration towards an atrium of the prosthetic mitral valve.

16. A method of implanting a prosthetic mitral valve assembly, comprising:
placing a purse string suture at an apex of a heart into which the mitral valve is to be implanted;
passing a guidewire through the apex of the heart at the suture location;
inserting a delivery catheter through the apex of the heart at the suture location, the delivery catheter including the prosthetic mitral valve assembly having a first pulmonary vein stent, a second pulmonary vein stent, a mitral valve stent, a first anchoring arm coupling the first pulmonary vein stent and the mitral valve stent, and a second anchoring arm coupled between the second pulmonary vein stent and the mitral valve stent;
passing the guidewire into a pulmonary vein;
advancing the first pulmonary vein stent from the delivery catheter into a first pulmonary vein such that a first end of the first anchoring arm is coupled to the first pulmonary vein stent;
radially expanding the first pulmonary vein stent to anchor it entirely within the first pulmonary vein;
advancing the second pulmonary vein stent from the delivery catheter into a second pulmonary vein such that a first end of the second anchoring arm is coupled to the second pulmonary vein stent;
radially expanding the second pulmonary vein stent to anchor it entirely within the second pulmonary vein;
positioning a mitral valve stent coupled to a second end of the first anchoring arm and a second end of the second anchoring arm in a native mitral valve so that the first anchoring arm and the second anchoring arm extends from adjacent the native mitral valve to the first pulmonary vein and the second pulmonary vein;
advancing the mitral valve stent from the delivery catheter;
radially expanding the mitral valve stent to anchor it within the native mitral valve; and
removing the delivery catheter and guidewire through the apex of the heart and closing the purse string suture.

17. The method of claim 16, wherein radially expanding the mitral valve stent comprises radially expanding an upper portion to contact a wall of a left atrium, radially expanding a tapered middle portion, and radially expanding a lower portion within an annulus of the mitral valve, wherein the lower portion has a circumference that is less than a circumference of the upper portion.

18. The method of claim 16, wherein the prosthetic mitral valve assembly comprises a prosthetic valve disposed in the mitral valve stent, the prosthetic valve comprising a plurality of pericardium leaflets.

19. The method of claim 16, further comprising releasing extension arms extending from a lower end of the mitral valve stent from engagement with the delivery catheter.

* * * * *